US009085636B2

(12) United States Patent
Brunner et al.

(10) Patent No.: US 9,085,636 B2
(45) Date of Patent: Jul. 21, 2015

(54) CETP FRAGMENTS

(75) Inventors: Sylvia Brunner, Vienna (AT); Mathias Gebhart, Vienna (AT); Erika Bilcikova, Bratislava (SK); Claudia Juno, Vienna (AT); Pola Linzmayer-Hirt, Wiener Neudorf (AT); Birgit Schuh, Vienna (AT)

(73) Assignee: AFFIRIS AG, Vienna (AT)

( * ) Notice: Subject to any disclaimer, the term of this patent is extended or adjusted under 35 U.S.C. 154(b) by 0 days.

(21) Appl. No.: 14/116,075

(22) PCT Filed: Jun. 11, 2012

(86) PCT No.: PCT/EP2012/061038
§ 371 (c)(1),
(2), (4) Date: Nov. 6, 2013

(87) PCT Pub. No.: WO2012/168486
PCT Pub. Date: Dec. 13, 2012

(65) Prior Publication Data
US 2014/0147456 A1     May 29, 2014

(30) Foreign Application Priority Data

Jun. 10, 2011    (EP) .................................... 11169481

(51) Int. Cl.
| | |
|---|---|
| C07K 9/00 | (2006.01) |
| C07K 14/47 | (2006.01) |
| C07K 16/18 | (2006.01) |
| A61K 39/00 | (2006.01) |
| A61K 38/08 | (2006.01) |
| A61K 38/04 | (2006.01) |
| A61P 9/10 | (2006.01) |
| A61K 38/00 | (2006.01) |

(52) U.S. Cl.
CPC ............. *C07K 14/47* (2013.01); *A61K 39/0005* (2013.01); *C07K 9/00* (2013.01); *C07K 16/18* (2013.01); *A61K 38/00* (2013.01); *A61K 38/04* (2013.01); *A61K 38/08* (2013.01); *A61K 2039/6081* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,410,022 B1 | 6/2002 | Rittershaus |
| 6,555,113 B1 | 4/2003 | Rittershaus et al. |
| 2002/0042364 A1 | 4/2002 | Rittershaus et al. |
| 2003/0108559 A1 | 6/2003 | Rittershaus et al. |

(Continued)

FOREIGN PATENT DOCUMENTS

| | | |
|---|---|---|
| WO | 96 34888 | 11/1996 |
| WO | 02 098915 | 12/2002 |

(Continued)

OTHER PUBLICATIONS

Krchnak et al (1995. Molecular Diversity. 1: 193-216).*

(Continued)

*Primary Examiner* — Zachary Howard
(74) *Attorney, Agent, or Firm* — Oblon, McClelland, Maier & Neustadt, L.L.P.

(57) ABSTRACT

The present invention relates to a peptide consisting of 6 to 20 amino acid residues and being derived from amino acid sequence VFKGTLKYGYTTAWWLGIDQSIDFEIDSAI (SEQ ID No. 23), wherein said peptide comprises amino acid sequence WWLGID (SEQ ID No. 24) and antibodies binding to these peptides.

12 Claims, 6 Drawing Sheets

(56) References Cited

U.S. PATENT DOCUMENTS

| | | |
|---|---|---|
| 2004/0087481 A1 | 5/2004 | Rittershaus et al. |
| 2006/0276400 A1 | 12/2006 | Adari et al. |
| 2011/0275556 A1 | 11/2011 | Brunner et al. |

FOREIGN PATENT DOCUMENTS

| | | |
|---|---|---|
| WO | 2006 133196 | 12/2006 |
| WO | 2009 021254 | 2/2009 |

OTHER PUBLICATIONS

Seubert et al (2008. Journal of Immunology. 180: 5402-5412).*
European Search Report Issued Sep. 9, 2011 in Application No. EP 11 16 9481 Filed Jun. 10, 2011.
International Preliminary Report on Patentability Issued May 21, 2013 in PCT/EP12/061038 Filed Jun. 11, 2012.
Written Opinion of the International Searching Authority Issued Sep. 28, 2012 in PCT/EP12/61038 Filed Jun. 11, 2012.
International Search Report Issued Sep. 28, 2012 in PCT/EP12/61038 Filed Jun. 11, 2012.
Roy, P., et al., "Structure-function relationships of human cholesteryl ester transfer protein: analysis using monoclonal antibodies", Journal of Lipid Research, vol. 37, No. 1, pp. 22-34, (1996) XP 002240080.
Clark, R.W., "Raising high-density lipoprotein with cholesteryl ester transfer protein inhibitors", Current Opinion in Pharmacology, vol. 6, No. 2, pp. 162-168, (2006) XP 28058520.
Stein, E.A., et al., "Safety and tolerability of dalcetrapib (RO4607381/JTT-705): results from a 48-week trial", European Heart Journal, pp. 1-9, (Jan. 22, 2010).
Cannon, C.P., et al., "Safety of Anacetrapib in Patients with or at High Risk for Coronary Heart Disease", The New England Journal of Medicine, pp. 1-10, (2010).
Nissen, E.N., et al., "Effect of Torcetrapib on the Progression of Coronary Atherosclerosis", The New England Journal of Medicine, vol. 356, No. 13, pp. 1304-1316, (Mar. 29, 2007).
Steinberg, D., "An interpretive history of the cholesterol controversy: part II: the early evidence linking hypercholesterolemia to coronary disease in humans", Journal of Lipid Research, vol. 46, pp. 179-190, (2005).
O'Hagan, D.T., et al., "Recent Advances in the Discovery and Delivery of Vaccine Adjuvants", Nature Reviews, vol. 2, pp. 727-735, (Sep. 2003).
Bird, R.E., et al., "Single-Chain Antigen-Binding Proteins", Reports, vol. 242, pp. 423-426, (Oct. 21, 1988).
Huston, J.S., et al., "Protein engineering of antibody binding sites: Recovery of specific activity in an anti-digoxin single-chain Fv analogue produced in *Escherichia coli*", Proc. Natl. Acad. Sci. USA, vol. 85, pp. 5879-5883, (Aug. 1988).
McCafferty, J., et al., "Phage antibodies: filamentous phage displaying antibody variable domains", Letters to Nature, vol. 348, pp. 552-554, (Dec. 6, 1990).
Martin, F., et al., "The affinity-selection of a minibody polypeptide inhibitor of human interleukin-6", The EMBO Journal, vol. 13, No. 22, pp. 5303-5309, (1994).
Holliger, P., et al., "Diabodies: Small bivalent and bispecific antibody fragments", Proc. Natl. Acad. Sci. USA, vol. 90, pp. 6444-6448, (Jul. 1993).
Traunecker, A., et al., "Biospecific single chain molecules (Janusins) target cytotoxic lymphocytes on HIV infected cells", The EMBO Journal, vol. 10, No. 12, pp. 3655-3659, (1991).
Hou, S., et al., "Humanization of an Anti-CD34 Monoclonal Antibody by Complementarity-determining Region Grafting Based on Computer-assisted Molecular Modelling", J. Biochem, vol. 144, pp. 115-120, (2008).
Singh, M., et al., "Advances in vaccine adjuvants", Nature Biotechnology, vol. 17, pp. 1075-1081, (Nov. 1999).
Ritterhaus, C.W., et al., "Vaccine-Induced Antibodies Inhibit CETP Activity In Vivo and Reduce Aortic Lesions in a Rabbit Model of Atherosclerosis", Arterioscler Thromb Vasc Biol., vol. 20, pp. 2106-2112, (2000).
Steinberg, D., "An interpretive history of the cholesterol controversy, part V: The discovery of the statins and the end of the controversy", Journal of Lipid Research, vol. 47, pp. 1339-1351, (2006).
Supplemental Data File, "Methods", pp. 1-5, (Jan. 22, 2010).
Eckardstein, A.V., "Mulling over the odds of CETP inhibition", European Heart Journal, pp. 1-4, (Jan. 22, 2010).
Krauss, R.M., et al., "Changes in Lipoprotein Subfraction Concentration and Composition in Healthy Individuals Treated with the Cholesteryl Ester Transfer Protein Inhibitor Anacetrapib", Journal of Lipid Research, pp. 1-34, (Jan. 31, 2012).
Luscher, T.F., et al., "Vascular effects and safety of dalcetrapib in patients with or at risk of coronary heart disease: the dal-VESSEL randomized clinical trial", European Heart Journal, pp. 1-11, (Feb. 16, 2012).
Ill, C.R., et al., "Design and construction of hybrid immunoglobulin domain with properties of both heavy and light chain variable regions", Protein Engineering, vol. 10, No. 8, pp. 949-957, (1997).
Thomas, L.J., et al., "Co-administration of a CpG adjuvant (VaxImmune™, CPG 7909) with CETP vaccines increased immunogenicity in rabbits and mice", Human Vaccines, vol. 5, No. 2, pp. 79-84, (Feb. 2009).
First Examination Report issued on Oct. 7, 2014 in the corresponding New Zealand Patent Application No. 613913.
Krchnak Viktor, et al., "Synthetic library techniques: Subjective (biased and generic) thoughts and views", Molecular Diversity, vol. 1, No. 3, May 1996, pp. 193-216.

* cited by examiner

CETP FRAGMENTS

The present invention relates to peptides which are able to influence the in vivo activity of CETP.

Diseases associated with atherosclerosis, such as cardiovascular disease (CVD) as well as stroke and peripheral arterial occlusion disease, are among the main causes of death in the United States, Europe, and in large parts of Asia. Compared to the year 1990, mortality from CVD will have increased by 90% in 2020

Various risk factors are held responsible for the forming of atherosclerotic lesions. Circulating lipoprotein profiles, arterial hypertension and abuse of nicotine are of particular significance in this respect.

In comprehensive epidemiologic studies, a positive correlation between the level of the serum cholesterol and the occurrence of coronary heart disease could be demonstrated. High Low Density Lipoprotein cholesterol (LDLc) levels constitute a high cardiovascular risk, and are directly correlating with increased risk for atherosclerosis. Statins as HMG-CoA Reductase inhibitors are commonly used and are successfully reducing circulating LDLc levels. However, despite reduction of coronary events due to aggressive statin treatment, considerable residual cardiovascular risk remains a challenge. Thus, new therapeutics are urgently needed.

Besides the level of the LDL cholesterol, also the level of the vessel-protecting High Density Lipoprotein cholesterol (HDLc) plays an important role when estimating the risk profile for cardiovascular diseases. Epidemiologic studies have demonstrated an inverse relationship between HDLc levels and atherosclerosis. HDLc levels are strong predictors independent from LDLc values. Therefore it is assumed that HDLc levels have atheroprotective effects. Elevating HDLc levels therefore is a major goal and additional target.

Monotherapy with statins does not efficaciously raise HDLc levels, treatment and prevention of atherosclerosis with this type of pharmacological compound is not sufficient. Current options for raising HDLc levels are fibrates and niacin. Especially niacin is effective, however its use is limited by adverse effects which lead to low compliance of patients. An efficacious and safe method for the raise of HDLc levels to complement LDL reduction by statins is urgently needed. In this respect, inhibition of CETP as monotherapy or as add-on therapy is an attractive goal.

Cholesterol ester transfer protein (CETP) is a plasma glycoprotein which is responsible for the transfer of neutral lipids, including cholesteryl ester and triglyceride (TG), between lipoproteins. Cholesteryl esters from atheroprotective HDL are transferred to pro-atherogenic apolipoprotein (apo) B lipoprotein (LDL and VLDL) in exchange for TG. This leads to lower levels of HDL and raises the levels of LDL and VLDL.

It is assumed that CETP, most likely depending on the metabolic background, is a valuable therapeutic target for the goal of increasing the HDL plasma level.

Many species do not have CETP. In species with susceptibility to atherosclerosis, such as rabbit and man, CETP activity is high. Others that are resistant to atherosclerosis do not possess CETP and have high HDLc levels.

In animal experiments with rabbits and hamsters, the transient inhibition of CETP with anti-CETP monoclonal antibodies, antisense oligonucleotides or CETP inhibitors led to the increase in the HDL levels.

Several classes of CETP inhibitors have been described, some of which are already in advanced clinical trials (e.g. dalcetrapib (Stein E A, Eur Heart J. 31(4) (2010):480-8) anacetrapib (Cannon C P, N Engl J Med. 363(25) (2010): 2406-15 and torcetrapib (Nissen S E, N Engl J Med. 356(13) (2007):1304-16).

In U.S. Pat. No. 5,512,548 and in WO 93/011782, polypeptides and their analogues are described which are capable of inhibiting CETP that catalyses the transfer of cholesterol esters from HDL to VLDL and LDL, and, therefore, have anti-atherosclerotic activity if administered to a patient. According to these documents, such a CETP polypeptide inhibitor is derived from apoC-I of various sources, wherein especially N-terminal fragments up to amino acid 36 have been identified as CETP inhibitors.

Also in U.S. Pat. No. 5,880,095 A, a CETP-binding peptide is disclosed which is capable of inhibiting the activity of CETP in an individual. The CETP-inhibitory protein comprises an N-terminal fragment of porcine apoC-III.

In US 2006/0276400 and WO 96/034888 peptides are disclosed, which are derived from CETP and comprise T-cell and/or B-cell epitopes. These peptides are able to induce in vivo the formation of CETP specific antibodies.

In US 2004/0087481 and U.S. Pat. No. 6,410,022 B1, peptides are disclosed which, because of the induction of a CETP-specific immune response, can be used for the treatment and prevention of cardiovascular diseases, such as, e.g., atherosclerosis. These peptides comprise a T helper cell epitope which is not derived from CETP, and at least one B-cell epitope that comes from CETP and can be derived directly from the latter. The T helper cell epitope advantageously is derived from tetanus toxoid and is covalently bound to at least one B-cell epitope of CETP. By using a T helper cell epitope that is alien to the organism, it becomes possible to induce antibodies in the body of an individual, which antibodies are directed against that peptide portion that consists of at least one CETP-B-cell epitope.

In WO 2006/029982 CETP mimotopes to be used for the manufacture of a medicament for the treatment or prevention of atherosclerosis is described.

There have already been suggestions for a vaccine approach with regard to CETP. Rabbits have been treated with a vaccine which contained a peptide derived from the C-terminus of CETP as an antigen. The immunized rabbits had a reduced CETP activity and altered lipoprotein levels with increased HDL and reduced LDL values. Moreover, the treated test animals of the atherosclerosis model also showed reduced atherosclerotic lesions in comparison with control animals (Rittershaus C W, Arterioscler Thromb Vasc Biol 20(2000): 2106-12).

The results of a phase II clinical study with the vaccine CETi-1, which was carried out by the American biotechnology company Avant, were published (BioCentury Extra For Wednesday, Oct. 22, 2003). In this phase II study, just as in the preceding phase I study, a very good safety profile without any questionable side effects was proven, allowing the conclusion to be drawn that no side effects are to be expected from an anti-CETP vaccination approach. With regard to efficacy, however, the Avant vaccine was disappointing since it did not lead to increased HDL levels significantly better than those attained by a placebo treatment.

It is an object of the present invention to provide means and methods for reducing the activity of CETP in an individual.

The present invention relates to a peptide consisting of 6 to 20 amino acid residues and being derived from amino acid sequence VFKGTLKYGYTTAWWLGIDQSIDFEIDSAI (SEQ ID No. 23), wherein said peptide comprises amino acid sequence WWLGID (SEQ ID No. 24)

It surprisingly turned out that peptides comprising the amino acid sequence WWLGID (SEQ ID NO: 24) are able to induce in a mammal, in particular in mouse, antibodies directed to CETP. These antibodies are able to bind to CETP and in addition are reducing the in vivo activity of said protein leading to an increase of the HDL levels in the mammal to which said peptides are administrated. The increase of the HDL levels in a mammal leads to an alleviation of atherosclerosis and other diseases associated with atherosclerosis, in particular cardiovascular diseases.

The peptides of the present invention comprising the amino acid sequence WWLGID (SEQ ID NO: 24) are derived from the peptide having the amino acid sequence VFKGTLKYGYTTAWWLGIDQSIDFEIDSAI (SEQ ID No. 23) which is a fragment of human CETP (Protein Data Bank Accession No. 2OBD_A GI:126031487). The peptide having the amino acid sequence SEQ ID No. 23 comprises amino acid residues 92 to 121 of the mature CETP protein. This CETP protein fragment and truncated variants thereof which comprise the amino acid sequence WWLGID (SEQ ID NO: 24) induce, as mentioned before, the formation of antibodies binding specifically to CETP. However, other fragments derived from CETP including amino acid residues 47 to 55, 152 to 165, 290 to 300, 300 to 316 and 403 to 415 of the mature CETP protein, although being present on the surface of the full-length CETP protein, do not lead to the formation of antibodies directed (i.e. binding) to the CETP protein, although the administration of such fragments to a mammal induces the formation of fragment specific antibodies. This is surprising since a person skilled in the art would obviously expect that CETP fragments exposed on the surface of the CETP protein would be necessary to induce the formation of antibodies directed to the CETP protein.

It is well known in the art that longer peptides show a higher probability to comprise one or more T-cell epitopes which are not desired in such a vaccine. Activation of cytotoxic T cell epitopes (CD4 and CD8) could lead to the induction of autoreactive T cells inducing unwanted adverse events (AEs). Therefore the skilled artisan—in order to avoid undesired epitopes in a vaccine—would use peptides as antigens which are as short as possible in order to induce an antigen specific humoral immune response. Therefore shorter peptides—besides the fact that shorter peptides can much more easily chemically synthesised—are preferred.

In WO 02/098915 polypeptides of less than 100 amino acids are disclosed which comprise amino acid sequence SEQ ID No. 23 of the present invention. The polypeptides of WO 02/098915 are used to produce antibodies directed to CETP. Due to the length of the peptides disclosed in WO 02/098915 also antibodies are induced which may not be useful to treat or prevent atherosclerosis and diseases associated with atherosclerosis because such antibodies might be specific for parts of CETP not relevant for its mode of action.

As used herein, the term "peptide" refers to a polymeric molecule having at least 6 amino acid residues which are linked to each other by peptide bonds.

The term "derived from", as used in the context of the peptides of the present invention, means that the peptides of the present invention are fragments of the peptide having the amino acid sequence SEQ ID No. 23. Therefore the term "derived from" can be used interchangeably with "being a fragment of".

According to a preferred embodiment of the present invention the peptide consisting of 6 to 20 amino acid residues and being derived from amino acid sequence VFKGTLKYGYTTAWWLGIDQSIDFEIDSAI (SEQ ID No. 23) may comprise or consist of 6 to 16 amino acid residues.

According to a particularly preferred embodiment of the present invention the peptide comprises 8 to 20, preferably 8 to 16, amino acid residues. If the peptides of the present invention comprise a C- and/or N-terminal cysteine residue the peptide may comprise 9 to 21, preferably 9 to 17, or 10 to 22, preferably 10 to 18, amino acid residues.

In case the peptide of the present invention comprises at least 8 consecutive amino acid residues of the amino acid sequence SEQ ID No. 23, said peptide preferably comprises or consists of amino acid sequence SEQ ID No. 10, SEQ ID No. 11, SEQ ID No. 18 and/or SEQ ID No. 19.

According to another preferred embodiment of the present invention the amino acid sequence of the peptide is selected from the group consisting of YTTAWWLGIDQS (SEQ ID No. 1), YGYTTAWWLGIDQSID (SEQ ID No. 7), TTAWWLGIDQS (SEQ ID No. 8), TAWWLGIDQS (SEQ ID No. 9), AWWLGIDQS (SEQ ID No. 10), WWLGIDQS (SEQ ID No. 11), YTTAWWLGIDQ (SEQ ID No. 13), YTTAWWLGID (SEQ ID No. 14), TTAWWLGIDQ (SEQ ID No. 18) and TTAWWLGID (SEQ ID No. 19), particularly preferred from the group consisting of TAWWLGIDQS (SEQ ID No. 9), AWWLGIDQS (SEQ ID No. 10) and WWLGIDQS (SEQ ID No. 11).

The peptides of the present invention can be chemically synthesised by methods which are well known in the art. Of course it is also possible to produce the peptides of the present invention using recombinant methods. The peptides can be produced in microorganisms such as bacteria, yeast or fungi, in eukaryotic cells such as mammalian or insect cells, or in a recombinant virus vector such as adenovirus, poxvirus, herpesvirus, Simliki forest virus, baculovirus, bacteriophage, sindbis virus or sendai virus. Suitable bacteria for producing the peptides include *E. coli, B. subtilis* or any other bacterium that is capable of expressing such peptides. Suitable yeast cells for expressing the peptides of the present invention include *Saccharomyces cerevisiae, Schizosaccharomyces pombe, Candida, Pichiapastoris* or any other yeast capable of expressing peptides. Corresponding means and methods are well known in the art. Also methods for isolating and purifying recombinantly produced peptides are well known in the art and include e.g. gel filtration, affinity chromatography, ion exchange chromatography etc.

To facilitate isolation of the peptides of the present invention, fusion polypeptides may be made wherein the peptides are translationally fused (covalently linked) to a heterologous polypeptide which enables isolation by affinity chromatography. Typical heterologous polypeptides are His-Tag (e.g. $His_6$ (SEQ ID NO: 112); 6 histidine residues (SEQ ID NO: 112)), GST-Tag (Glutathione-S-transferase) etc. The fusion polypeptide facilitates not only the purification of the peptides but can also prevent the degradation of the peptides during the purification steps. If it is desired to remove the heterologous polypeptide after purification, the fusion polypeptide may comprise a cleavage site at the junction between the peptide and the heterologous polypeptide. The cleavage site may consist of an amino acid sequence that is cleaved with an enzyme specific for the amino acid sequence at the site (e.g. proteases).

The peptides of the present invention may also comprise at their N- and/or C-terminus a cysteine residue bound thereto.

The provision of a cysteine residue at the N- and/or C-terminus of a peptide may facilitate its conjugation to a carrier and/or may enhance the immunogenicity of the peptide. If a cystein residue is added to the C- and/or N-terminus of the peptides of the present invention, the number of amino acid residues mentioned herein increases obviously for 1 or 2 amino acid residues. Therefore the peptide of consisting of 6 to 20 amino acid residues and being derived from amino acid sequence VFKGTLKYGYTTAWWLGIDQSIDFEIDSAI (SEQ ID No. 23), wherein said peptide comprises amino acid sequence WWLGID (SEQ ID No. 24), may the consist of 7 to 21 or 8 to 22 amino acid residues.

Particularly preferred peptides of the present invention having a C- or N-terminal cysteine residue are selected from the group consisting of C-YTTAWWLGIDQS (SEQ ID NO: 113), C-YGYTTAWWLGIDQSID (SEQ ID NO: 114), C-TTAWWLGIDQS (SEQ ID NO: 115), C-TAWWLGIDQS (SEQ ID NO: 116), C-AWWLGIDQS (SEQ ID NO: 117), C-WWLGIDQS (SEQ ID NO: 118), C-YTTAWWLGIDQ (SEQ ID NO: 119), C-YTTAWWLGID (SEQ ID NO: 120), C-TTAWWLGIDQ (SEQ ID NO: 121) and TTAWWLGID-C (SEQ ID NO: 122).

According to a preferred embodiment of the present invention the peptide is used for preventing and/or treating atherosclerosis and diseases associated with atherosclerosis.

As outlined above, the peptides of the present invention are able to induce the formation of antibodies which are able to bind specifically CETP particularly present in humans. The binding of these antibodies to CETP leads to a reduction of the activity of CETP in vivo. As a consequence thereof the level of HDL is increased.

The disease associated with atherosclerosis is preferably selected from the group consisting of peripheral arterial occlusive disease, coronary heart disease, apoplectic cerebral insultus and stroke.

The term "diseases associated with atherosclerosis" refers to diseases which are a consequence of atherosclerosis. These diseases include among others peripheral arterial occlusive disease, coronary heart disease and apoplectic cerebral insultus (see e.g. Steinberg D., J. Lipid Res. 46 (2005): 179-190; Steinberg D et al., J. Lipid Res. 47 (2006): 1339-1351).

According to a preferred embodiment of the present invention the peptide is administered to an individual in an amount of 0.5 to 500 μg, preferably 1 to 100 μg, per immunization. However, the peptide of the present invention may alternatively be administered to an individual in an amount of 0.1 ng to 10 mg, preferably 10 ng to 1 mg, in particular 100 ng to 300 μg/kg body weight.

The amount of peptides that may be combined with the carrier materials to produce a single dosage form will vary depending upon the host treated and the particular mode of administration. The dose of the vaccine may vary according to factors such as the disease state, age, sex and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the peptides and vaccine of the present invention may be administered to an individual at intervals of several days, one or two weeks or even months depending always on the level of antibodies directed to CETP.

In a preferred embodiment of the present invention the peptide/vaccine is applied between 2 and 10, preferably between 2 and 7, even more preferably up to 5 and most preferably up to 3 times. In a particularly preferred embodiment the time interval between the subsequent vaccinations is chosen to be between 2 weeks and 5 years or more, preferably between 1 month and up to 3 years, more preferably between 2 months and 1.5 years. The repeated administration of the peptide/vaccine of the present invention may maximize the final effect of a therapeutic vaccination.

Another aspect of the present invention relates to a vaccine comprising at least one peptide as defined above comprising 6 to 30 amino acid residues and being derived from amino acid sequence VFKGTLKYGYTTAWWLGIDQSID-FEIDSAI (SEQ ID No. 23), wherein said peptide comprises amino acid sequence WWLGID (SEQ ID No. 24).

The vaccine of the present invention may comprise one or more, preferably 2, 3, 4, 5, 6, 7, 8, 9 or 10, of the peptides selected from the group consisting of YTTAWWLGIDQS (SEQ ID No. 1), YGYTTAWWLGIDQSID (SEQ ID No. 7), TTAWWLGIDQS (SEQ ID No. 8), TAWWLGIDQS (SEQ ID No. 9), AWWLGIDQS (SEQ ID No. 10), WWLGIDQS (SEQ ID No. 11), YTTAWWLGIDQ (SEQ ID No. 13), YTTAWWLGID (SEQ ID No. 14), TTAWWLGIDQ (SEQ ID No. 18) and TTAWWLGID (SEQ ID No. 19).

Particularly preferred combinations of peptides include: SEQ ID No. 10 and 11; SEQ ID No. 8 and 9; SEQ ID No. 8 and 10; SEQ ID No. 8 and 11; SEQ ID No. 9 and 10; SEQ ID No. 9 and 11; SEQ ID No. 8, 9 and 10; SEQ ID No. 8, 9 and 11; SEQ ID No. 8, 9, 10 and 11; SEQ ID No. 10, 11 and 18; SEQ ID No. 8, 9 and 18; SEQ ID No. 8, 10 and 18; SEQ ID No. 8, 11 and 18; SEQ ID No. 9, 10 and 18; SEQ ID No. 9, 11 and 18; SEQ ID No. 8, 9, 10 and 18; SEQ ID No. 8, 9, 11 and 18; SEQ ID No. 8, 9, 10, 11 and 18; SEQ ID No. 8 and 18; SEQ ID No. 9 and 18; SEQ ID No. 10 and 18; SEQ ID No. 11 and 18.

The vaccine of the present invention may also comprise other peptidic fragments of CETP or variants thereof or any other peptides which are able to induce the in vivo formation of antibodies directed to CETP, particularly human CETP. Particularly suited are the peptides disclosed in WO 2009/021254. The peptides disclosed therein have amino acid sequence $FX_8(F)_oPX_9HX_{10}X_{11}X_{12}DX_2X_3X_4X_5X_6X_7$ (SEQ ID NO: 25), wherein $X_8$ is selected from the group consisting of G, A, F, Y and K, $X_9$ is selected from the group consisting of E, Y, A, Q, K and S, $X_{10}$ is selected from the group consisting of H, V, L, F and I, $X_{11}$ is selected from the group consisting of L, W, S, I, F and Y, $X_{12}$ is V, T, F or I, $X_2$ is an amino acid residue selected from the group consisting of F, A, W, R, S, L, Q, V and M, $X_3$ is an amino acid residue selected from the group consisting of L, A, S, W, E, R, I and H, $X_4$ is an amino acid residue selected from the group consisting of Q, A, H, D, K, R, S and E, $X_5$ is S or Y, $X_6$ is L, A or I, $X_7$ is S, N or T, and o is 0 or 1. Preferred combinations comprise the peptides of the present invention and one or more peptides selected from the group consisting of FGFPEHLLVD-FLQSLS (SEQ ID NO: 26), FPEHLLVDFLQSL (SEQ ID NO: 27), AGFPEHLLVDFLQSLS (SEQ ID NO: 28), FAF-PEHLLVDFLQSLS (SEQ ID NO: 29), FGAPEHLLVD-FLQSLS (SEQ ID NO: 30), FGFAEHLLVDFLQSLS (SEQ ID NO: 31), FGFPAHLLVDFLQSLS (SEQ ID NO: 32), FGFPEALLVDFLQSLS (SEQ ID NO: 33), FGFPEHALVD-FLQSLS (SEQ ID NO: 34), FGFPEHLAVDFLQSLS (SEQ ID NO: 35), FGFPEHLLADFLQSLS (SEQ ID NO: 36), FGFPEHLLVAFLQSLS (SEQ ID NO: 37), FGFPE-HLLVDALQSLS (SEQ ID NO: 38), FGFPEHLLVD-FAQSLS (SEQ ID NO: 39), FGFPEHLLVDFLASLS (SEQ ID NO: 40), FGFPEHLLVDFLQALS (SEQ ID NO: 41), FGFPEHLLVDFLQSAS (SEQ ID NO: 42), FGFPEHLLVD-FLQSLA (SEQ ID NO: 43), FAFPAHLLVDFLQALA (SEQ ID NO: 44), FGFPGHLIWDSLHSLS (SEQ ID NO: 45), FGFPYHHLVDQLHSLS (SEQ ID NO: 46), FGFPYH-VQVDVLQSLS (SEQ ID NO: 47), FGFPSHHLQD-SLQSLS (SEQ ID NO: 48), FGFPLHFRSDRIQSLS (SEQ ID NO: 49), FGFPKHLYADMSQSLS (SEQ ID NO: 50), FGFPAHLSRDLRQSLS (SEQ ID NO: 51), FGFPFHFAQD-SWQSLS (SEQ ID NO: 52), FGFPQHLTTDWAQSLS (SEQ ID NO: 53), FGFPQHLTTDWAQSLS (SEQ ID NO: 54), FGFPQHLTTDRLQSLS (SEQ ID NO: 55), FGFPQHLTTDWLQSLS (SEQ ID NO: 56), ATPSHLIIDRAQ (SEQ ID NO: 57), ATPSHLIIDRAQSLS (SEQ ID NO: 58), FGFPSHLIIDRAQSLS (SEQ ID NO: 59), FGFPSHLIIDWAQSLS (SEQ ID NO: 60), FGFPSHLIIDWLQSLS (SEQ ID NO: 61), FGFPSHLIIDWSQSLS (SEQ ID NO: 62), FAFPAHVSIDWLQSLS (SEQ ID NO: 63), FGFPAHVSIDWLQLLS (SEQ ID NO: 64), FGFPAHVSIDWLQWLS (SEQ ID NO: 65), FGFPAHVSIDWLQNLS (SEQ ID NO: 66), FGFPAHVSIDWLQTLS (SEQ ID NO: 67), FGFPAHVSIDWLQYLS (SEQ ID NO: 68), FGFPAHVSIDWLQSIS (SEQ ID NO: 69), FGFPAHVSIDWLQSLT (SEQ ID NO: 70), FGFPAHVSIDWLQSLY (SEQ ID NO: 71), FAFPAHVSIDWLQALA (SEQ ID NO: 72), FGFPAHVSIDRAQSLS (SEQ ID NO: 73), FGFPTHVSIDWLQSLS (SEQ ID NO: 74), FGFPFHVSIDWLQSLS (SEQ ID NO: 75), FGFPAHISIDWLQSLS (SEQ ID NO: 76), FGFPAHIIIDWLQSLS (SEQ ID NO: 77), FGFPAHLTTDWLQSLS (SEQ ID NO: 78), FGFPAHVFIDWLQSLS (SEQ ID NO: 79), FGFPAHVYIDWLQSLS (SEQ ID NO: 80), FGFPAHVSLDWLQSLS (SEQ ID NO: 81), FGFPAHVSADWLQSLS (SEQ ID NO: 82), FGFPAHVWIDWLQSLS (SEQ ID NO: 83), FGFPAHVFIDWLQSLN (SEQ ID NO: 84), FGFPAHFSIDWLQSLS (SEQ ID NO: 85), FGFPAHVSFDWLQSLS (SEQ ID NO: 86), FGFPEHVFIDWLQSLS (SEQ ID NO: 87), FGFPQHLFTDWLQSLS (SEQ ID NO: 88), FGFPKHLLVDFLQSLS (SEQ ID NO: 89), FGFPAHVSIDWSQSLS (SEQ ID NO: 90), FGFPAHVSIDFSQSLS (SEQ ID NO: 91), FGFPSHIIIDWLQSLS (SEQ ID NO: 92), FGFPSHLIIEWLQSLS (SEQ ID NO: 93), FAFPAHVFIDWLQSLS (SEQ ID NO: 94), FGFPAHVFIDWLQALS (SEQ ID NO: 95), FGFPAHVFIDWLQSLA (SEQ ID NO: 96), FAFPAHVFIDWLQALA (SEQ ID NO: 97), FGFPEHLFVDFLQSLS (SEQ ID NO: 98), FGFPAHVHIDWLQSLS (SEQ ID NO: 99), FGFPAHVPIDWLQSLS (SEQ ID NO: 100), FGFPSHLFIDWAQSLS (SEQ ID NO: 101), FGFPAHVYIDWLQ (SEQ ID NO: 102) and FGFPAHVFIDWLQ (SEQ ID NO: 103).

The vaccine of the present invention may also comprise antigens derived from other proteins which are also involved in the regulation of the LDL and/or HDL levels within a human body. For instance, the CETP fragments of the present invention may be combined with epitopes derived from PCSK9 (proprotein convertase subtilisin/kexin type 9) as disclosed in WO 2008/125623, WO 2010/057242 and WO 2011/027257.

According to a preferred embodiment of the present invention the at least one peptide is coupled or fused to a pharmaceutically acceptable carrier, preferably KLH (Keyhole Limpet Hemocyanin).

According to a preferred embodiment of the present invention the peptide is coupled or fused to a pharmaceutically acceptable carrier, preferably KLH (Keyhole Limpet Hemocyanin), tetanus toxoid, albumin-binding protein, hepatitis B core antigen, bovine serum albumin, a dendrimer (MAP), peptide linkers (or flanking regions), or CRM, preferably CRM197, as well as combined with adjuvant substances described in Singh et al., Nat. Biotech. 17 (1999): 1075-1081 (in particular those in Table 1 of that document), and O'Hagan et al., Nature Reviews, Drug Discovery 2(9) (2003): 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxide. Of course, also adjuvants like MF59 aluminium phosphate, calcium phosphate, cytokines (e.g. IL-2, IL-12, GM-CSF), saponins (e.g. QS21), MDP derivatives, CpG oligonucleotides, LPS, MPL, polyphosphazenes, emulsions (e.g. Freund's, SAF), liposomes, lipopeptides, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used.

The peptides of the present invention are preferably bound to the carrier or adjuvant via a linker, which is selected from the group consisting of NHS-poly(ethylene oxide) (PEO) (e.g. NHS-PEO$_4$-maleimide).

A vaccine which comprises a peptide of the present invention and the pharmaceutically acceptable carrier may be administered by any suitable mode of application, e.g. intradermally (i.d.), intravenously (i.v.), intraperitoneally (i.p.), intramuscularly (i.m.), intranasally, orally, subcutaneously (s.c.), etc. and in any suitable delivery device (O'Hagan et al., Nature Reviews, Drug Discovery 2(9) (2003): 727-735). The compound of the present invention is preferably formulated for s.c., i.d. or i.m. administration (see e.g. "Handbook of Pharmaceutical Manufacturing Formulations", Sarfaraz Niazi, CRC Press Inc, 2004).

The vaccine according to the present invention comprises at least one peptide which is preferably formulated for i.d., s.c., or i.m. administration.

At least one peptide in the vaccine is preferably formulated with an adjuvant, preferably aluminium hydroxide.

Typically, the vaccine contains the peptide according to the present invention in an amount of 0.5 to 500 µg, preferably 1 to 100 µg and alternatively from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

According to a particularly preferred embodiment of the present invention the vaccine may comprise two or more of the following components:

| | |
|---|---|
| antigen: amount of peptide per dosis | 0.1 µg to 1 mg, preferably 0.5 µg to 500 µg, more preferably 1 µg to 100 µg, net peptide |
| carrier | anything known to a person skilled in the art that is pharmaceutically and medically acceptable |
| carrier per dosis | 0.1 µg to 50 mg carrier |
| adjuvant/amount per dosis | anything that is medically and pharmaceutically acceptable |
| injection volume | anything that is medically acceptable (also depending on route of application) |
| buffer | anything that is medically and pharmaceutically acceptable |

According to a preferred embodiment of the present invention the vaccine is used for preventing and/or treating of atherosclerosis and diseases associated with atherosclerosis, wherein the disease associated with atherosclerosis is preferably selected from the group consisting of peripheral arterial occlusive disease, coronary heart disease, apoplectic cerebral insultus and stroke.

Another aspect of the present invention relates to the use of at least one peptide according to the present invention for the manufacture of a vaccine for preventing and/or treating of atherosclerosis and diseases associated with atherosclerosis.

Yet another aspect of the present invention relates to a method for treating an individual suffering or at risk to suffer from atherosclerosis or a disease associated with atherosclerosis in the course of which a peptide or vaccine according to the present invention is administered to said individual.

Next to the vaccine of the present invention, the individual to be treated may receive also other active ingredients known to influence the LDL and/or HDL levels in humans and mammals such as statins, fibrates, nicotinic acid, cholesterol uptake inhibitor (e.g. ezetimibe), ApoA1 Milano, delipidated HDL, plant sterols, PCSK9 inhibitors etc.

"Treating" as used herein means to cure an already present disease state or condition. Treating can also include inhibiting, i.e. arresting the development of a disease state or condition, and ameliorating, i.e. causing regression of a disease.

The term "preventing" as used herein means to completely or almost completely stop a disease state or condition from occurring in a patient or subject, especially when the patient or subject is predisposed to such a risk of contracting a disease state or condition.

Another aspect of the present invention relates to antibodies binding to or being directed to a peptide of the present invention consisting of 6 to 20 amino acid residues and being derived from amino acid sequence VFKGTLKYGYTTAWWLGIDQSIDFEIDSAI (SEQ ID No. 23), wherein said peptide comprises amino acid sequence WWLGID (SEQ ID No. 24).

Antibodies directed to the peptides of the present invention can be used to inhibit the CETP activity in a human or animal body. Therefore these antibodies can be used for passive vaccination of humans and animals.

The antibodies according to the present invention, which may be monoclonal or polyclonal, can be manufactured as known in the art. Monoclonal antibodies can be produced by a variety of techniques, including conventional monoclonal antibody methodology, for example the standard somatic cell hybridization technique of Kohler and Milstein (1975) Nature 256: 495. Other techniques for producing monoclonal antibodies can also be employed such as viral or oncogenic transformation of B lymphocytes.

According to a preferred embodiment the antibody comprises a heavy chain variable ("VH") region and an antibody light chain variable ("VL") region, each region comprising complementary determining regions, wherein the complementary determining regions of the VH region have one or more of the amino acid sequences NVQLQESGPGLVKPSQSLSLTCTVTGHSITSDYAWNWIRQFPGNKLEWMGYITNSGSTTYNPSLKSRISITRDTSKNQFFLQLNSVTTEDTATYYCTRGGPYWGQGTLVTVSA (SEQ ID No. 104), EVQLVESGGGLVEPGGSLKLSCVASGFTFSTYAMSWFRLTPERRLEWVAAISNGGSQNSYPDSVKGRFTVSRDNAKNTLYLQMSSLRSEDTAMYYCSRNGNYFDYWGQGTTLTVSS (SEQ ID No. 105), DVQLQESGPGLVKPSQSLSLTCTVTGYSITSDYAWNWIRQFPGNKLEWMGYISYSGTTTYNPSLKSRISITRHTSKNQFFLQLNSVTTEDSATYYCTRLGYYFDYWGQGTTLTVSS (SEQ ID No. 106) or QIQLVQSGPELKKPGETVKISCKASGYTFTDCSMHWVKQAPGQGLKWMGWINTKTGEPTYADDFKGRFAFSLETSASTAYLQINILKNEDSATYFCAAHSGKDYAIDYWGQGTSVTVSS (SEQ ID No. 107) and the VL region have one or more of the amino acid sequences DIVMTQSQKFMSTSVGDRVSITCKASQNVGTAVVWYQQKPGQSPKLLIYSASNRYTGVPDRFTGSGSGTDFTLTITNMQSEDLADYFCQQYSSYPLTFGAGTKLELK (SEQ ID No 108), QIVLTQSPAIMSASPGEKVTMTCSASSSISYMHWYQQKPGTSPKRWIFDTSKLASGVPARFSGSGSGTSYSLTISSMEAEDAATYYCHQRSSYPTFGSGTKLEIK (SEQ ID No. 109), DIVMTQSPASLAMSVGQKVTMNCKSSQSLLSSKNQKNFLAWYQQKPGQSPKVLVYFASTRASGVPDRFIGSGSGTDFTLTISSVQAEDLADYFCQQQYNTPLTFGAGTKLELK (SEQ ID No. 110) or DVLMTQTPLSLPVSLGDQASISCRSSQSIVHRNGNTYLEWYLQKPGQSPKLLIYKVSNRFSGVPDRFSGSGSGTDFTLRISRVEAQDLGVYFCFQGSRVPPTFGGGTKLEIK (SEQ ID No. 111).

Particularly preferred are antibodies comprising a VH region comprising NVQLQESGPGLVKPSQSLSLTCTVTGHSITSDYAWNWIRQFPGNKLEWMGYITNSGSTTYNPSLKSRISITRDTSKNQFFLQLNSVTTEDTATYYCTRGGPYWGQGTLVTVSA (SEQ ID No. 104) in combination with a VL region comprising DIVMTQSQKFMSTSVGDRVSITCKASQNVGTAVVWYQQKPGQSPKLLIYSASNRYTGVPDRFTGSGSGTDFTLTITNMQSEDLADYFCQQYSSYPLTFGAGTKLELK (SEQ ID No 108), or a VH region comprising EVQLVESGGGLVEPGGSLKLSCVASGFTFSTYAMSWFRLTPERRLEWVAAISNGGSQNSYPDSVKGRFTVSRDNAKNTLYLQMSSLRSEDTAMYYCSRNGNYFDYWGQGTTLTVSS (SEQ ID No. 105), in combination with a VL region comprising QIVLTQSPAIMSASPGEKVTMTCSASSSISYMHWYQQKPGTSPKRWIFDTSKLASGVPARFSGSGSGTSYSLTISSMEAEDAATYYCHQRSSYPTFGSGTKLEIK (SEQ ID No. 109), or a VH region comprising DVQLQESGPGLVKPSQSLSLTCTVTGYSITSDYAWNWIRQFPGNKLEWMGYISYSGTTTYNPSLKSRISITRHTSKNQFFLQLNSVTTEDSATYYCTRLGYYFDYWGQGTTLTVSS (SEQ ID No. 106) in combination with a VL region comprising DIVMTQSPASLAMSVGQKVTMNCKSSQSLLSSKNQKNFLAWYQQKPGQSPKVLVYFASTRASGVPDRFIGSGSGTDFTLTISSVQAEDLADYFCQQQYNTPLTFGAGTKLELK (SEQ ID No. 110), or a VH region comprising QIQLVQSGPELKKPGETVKISCKASGYTFTDCSMHWVKQAPGQGLKWMGWINTKTGEPTYADDFKGRFAFSLETSASTAYLQINILKNEDSATYFCAAHSGKDYAIDYWGQGTSVTVSS (SEQ ID No. 107) in combination with a VL region comprising DVLMTQTPLSLPVSLGDQASISCRSSQSIVHRNGNTYLEWYLQKPGQSPKLLIYKVSNRFSGVPDRFSGSGSGTDFTLRISRVEAQDLGVYFCFQGSRVPPTFGGGTKLEIK (SEQ ID No. 111).

To create a single chain antibody (scFv), the VH- and VL-encoding DNA fragments are operatively linked to another fragment encoding a flexible linker, such that the VH and VL sequences can be expressed as a contiguous single-chain protein, with the VL and VH domains joined by the flexible linker (e.g. Bird et al., Science 242:423-426 (1988); Huston et al., Proc. Natl. Acad. Sci. USA 85:5879-5883 (1988); McCafferty et al., Nature 348:552-554 (1990)). The single chain antibody may be monovalent, if only a single VH and VL are used, bivalent, if two VH and VL are used, or polyvalent, if more than two VH and VL are used. Bispecific or polyvalent antibodies may be generated that bind specifically to CETP and to another molecule.

In another aspect, other modified antibodies may be prepared using antibody encoding nucleic acid molecules. For instance, "Kappa bodies" (Ill et al., Protein Eng. 10: 949-57 (1997)), "Minibodies" (Martin et al., EMBO J. 13: 5303-9 (1994)), "Diabodies" (Holliger et al., Proc. Natl. Acad. Sci. USA 90: 6444-6448 (1993)), or "Janusins" (Traunecker et al., EMBO J. 10:3655-3659 (1991) and Traunecker et al., Int. J. Cancer (Suppl.) 7:51-52 (1992)) may be prepared using standard molecular biological techniques following the teachings of the specification.

The antibody of the present invention is preferably humanised. Methods to obtain such antibodies are well known in the art. One method is to insert the variable regions disclosed herein into a human antibody scaffold (see e.g. Hou S, et al. J Biochem 144 (2008): 115-20).

The present invention is further illustrated in the following figures and examples, however, without being restricted thereto.

FIG. 1 shows median anti-peptide (FIG. 1A) and median anti-protein titers (n=5 mice per group) (FIG. 1B) for peptides with SEQ ID Nos 1 to 6 and 22 delineated from the CETP amino acid sequence. FIG. 1A and 1B each disclose the full-length peptides as SEQ ID NOS 113 and 123-128, respectively, in order of appearance.

FIG. 2 shows median anti-peptide (FIG. 2A) and median anti-protein titers (FIG. 2B) (n=5 mice per group) for peptides with SEQ ID No. 1 and 7 to 21 (truncated peptides). FIG. 2A discloses the full-length peptides as SEQ ID NOS 113, 113-118, 129, 119-120, 130-132, 121-122 and 133-134, respectively, in order of appearance. FIG. 2B discloses the full-length peptides as SEQ ID NOS 113-118, 129, 119-120, 130-132, 121-122 and 133-134, respectively, in order of appearance.

FIG. 3 discloses the full-length peptides as SEQ ID NOS 113-118, 129, 119-120, 130-132, 121-122 and 133-134, respectively, in order of appearance.

EXAMPLES

Materials and Methods

Vaccine

Figure 1A:
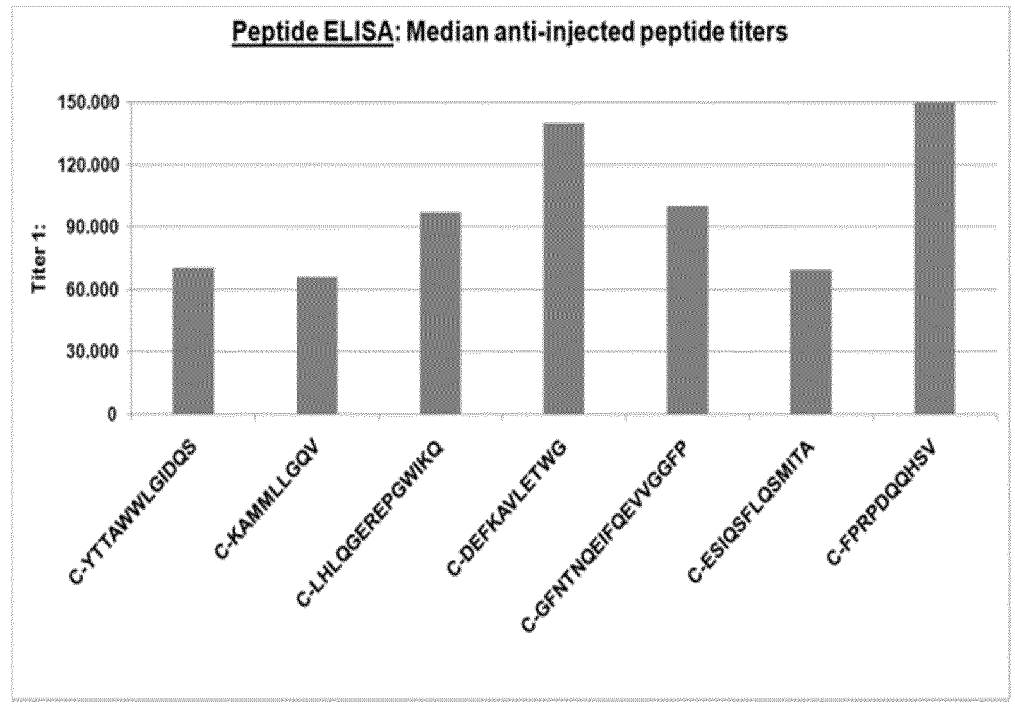

The peptides were conjugated via the heterobifunctional linker GMBS (4-Maleimidobutyric acid N-hydroxysuccinimide ester) to KLH (Keyhole Limpet Hemocyanin).

15 µg of the peptides were suspended with aluminum hydroxide (end concentration of aluminum hydroxide was 0.2%). As buffer mannitol/phosphate was used.

Animal Experiments

5 Balb/c mice were subcutaneously immunized. Mice had access to food and water ad libitum and were kept under a 12 h light/dark cycle. Age of mice at the beginning of experiments was usually 8 to 10 weeks.

Mice were injected three times in 2 week intervals with 15 µg of net peptide coupled to KLH and adsorbed to Alum as adjuvant in a volume of 1 ml in total via the s.c. route.

Blood was taken approximately 2 weeks after the final injection.

Peptide ELISA

To determine the immunogenicity of the vaccines, 96-well Nunc-Maxisorb plates were coated with 1 µM of the respective peptides coupled to bovine serum albumin (BSA) in 0.1 M NaHCO₃, pH 9.2-9.4. An irrelevant peptide was used as negative control. KLH was included as positive control and coated at a concentration of 1 µg/ml. Unspecific binding was blocked by incubation with blocking buffer (5% BSA in PBS). Appropriate serum dilutions were added to the wells, serially diluted 1:2 fold and incubated for approximately 1 hour at 37° C. On every ELISA plate a standard serum was included as internal control. Bound antibodies were detected by incubation with biotinylated goat anti-mouse IgG, followed by horseradish peroxidase coupled to Streptavidin. As substrate ABTS was added and the optical density (OD) at 405 nm was measured in a Microwell plate-reader. The titres were defined as the dilution of the serum where 50% of the ODmax in the assay are reached.

Protein ELISA

The antibodies induced by the vaccination were tested for their ability to bind to recombinantly expressed human CETP N-terminally fused to GST ("GST-CETP") using the protocol described under "peptide ELISA".

CETP Activity Inhibition Assay

CETP activity was determined with the Roar CETP activity assay kit (RB-CETP; Roar Biomedical) by measuring the transfer of a fluorescently labeled substrate according to the protocol provided by the manufacturer. Mice do not have endogenous CETP activity, therefore a modification of this protocol was introduced. Human serum was used as CETP source and was mixed with the same amount of serum from vaccinated mice together with donor and acceptor particles (components of the CETP activity assay kit).

Mouse sera containing CETP-inhibiting antibodies lead to a decrease of the signal in this assay. Sera from mice injected with irrelevant peptide served as negative control.

For testing of inhibition by monoclonal antibodies, indicated amounts of purified antibodies were added to the human serum.

Example 1

Comparison of Several Potential CETP Epitopes

| SEQ ID No. (truncated peptides) | SEQ ID NO: (full-length peptides) | amino acid sequence | position within the mature CETP protein |
|---|---|---|---|
| 1 | 113 | C-YTTAWWLGIDQS | AA101-112 |
| 2 | 123 | C-KAMMLLGQV | AA47-55 |
| 3 | 124 | C-LHLQGEREPGWIKQ | AA152-165 |
| 4 | 125 | C-DEFKAVLETWG | AA290-300 |
| 5 | 126 | C-GFNTNQEIFQEVVGGFP | AA300-316 |
| 6 | 127 | C-ESIQSFLQSMITA | AA403-415 |
| 22 | 128 | C-FPRPDQQHSV | AA350-359 |

Figure 1B:
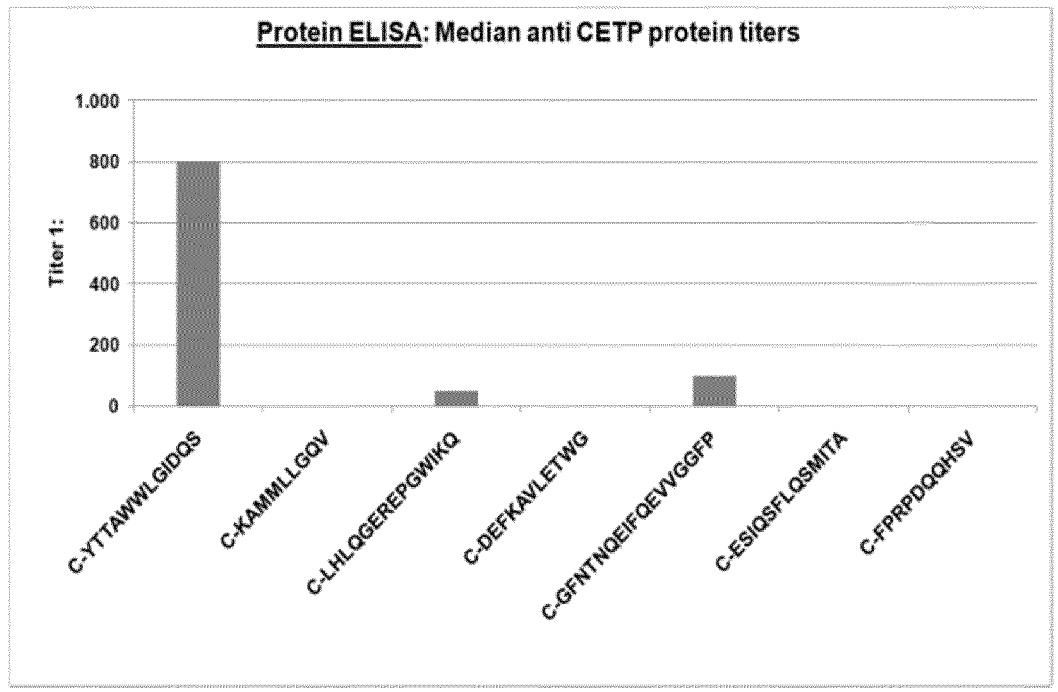
Figure 2A:
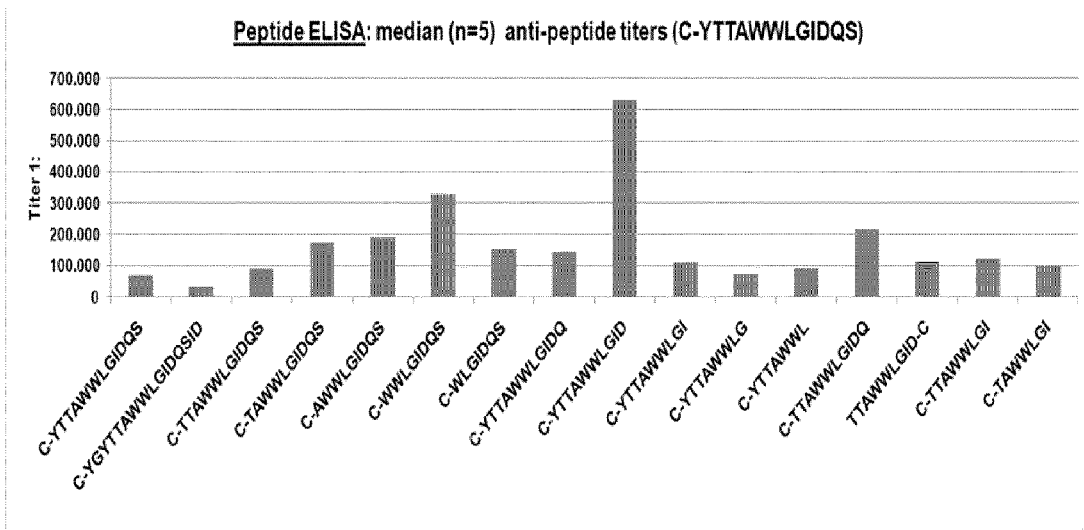
Figure 2B:
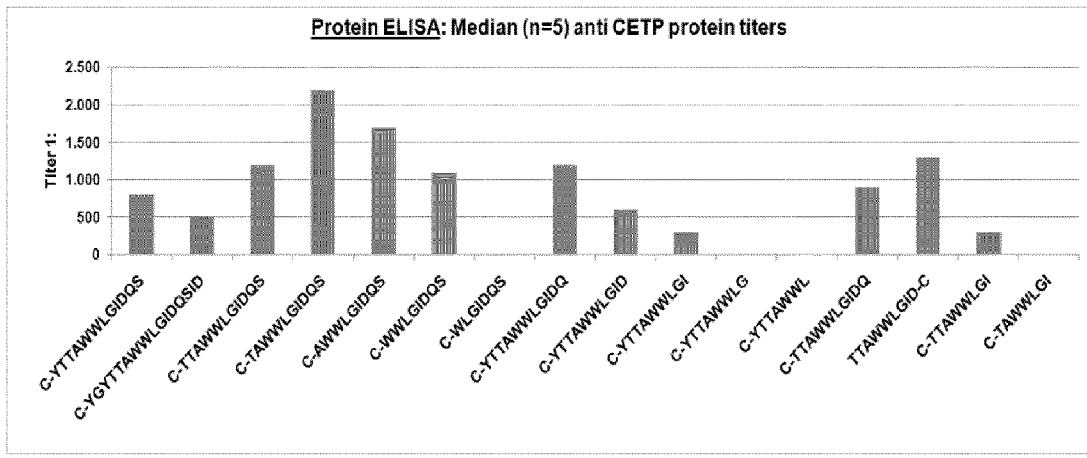
Figure 3:
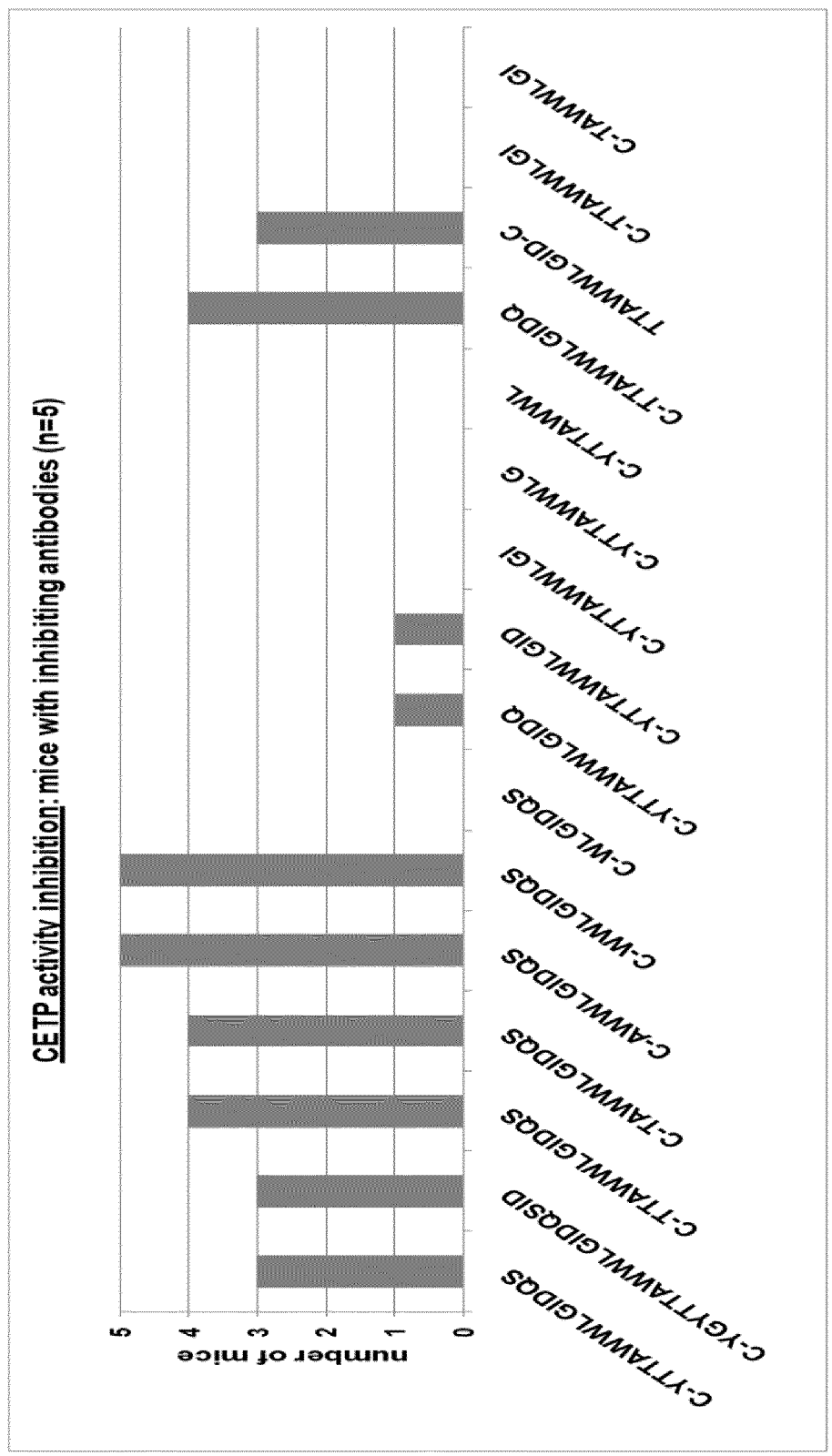
FIG. 3 shows the number of mice with antibodies inhibiting CETP activity (n=5 mice per group) for peptides with SEQ ID No. 1 and 7 to 21 (truncated peptides).
Figure 4:
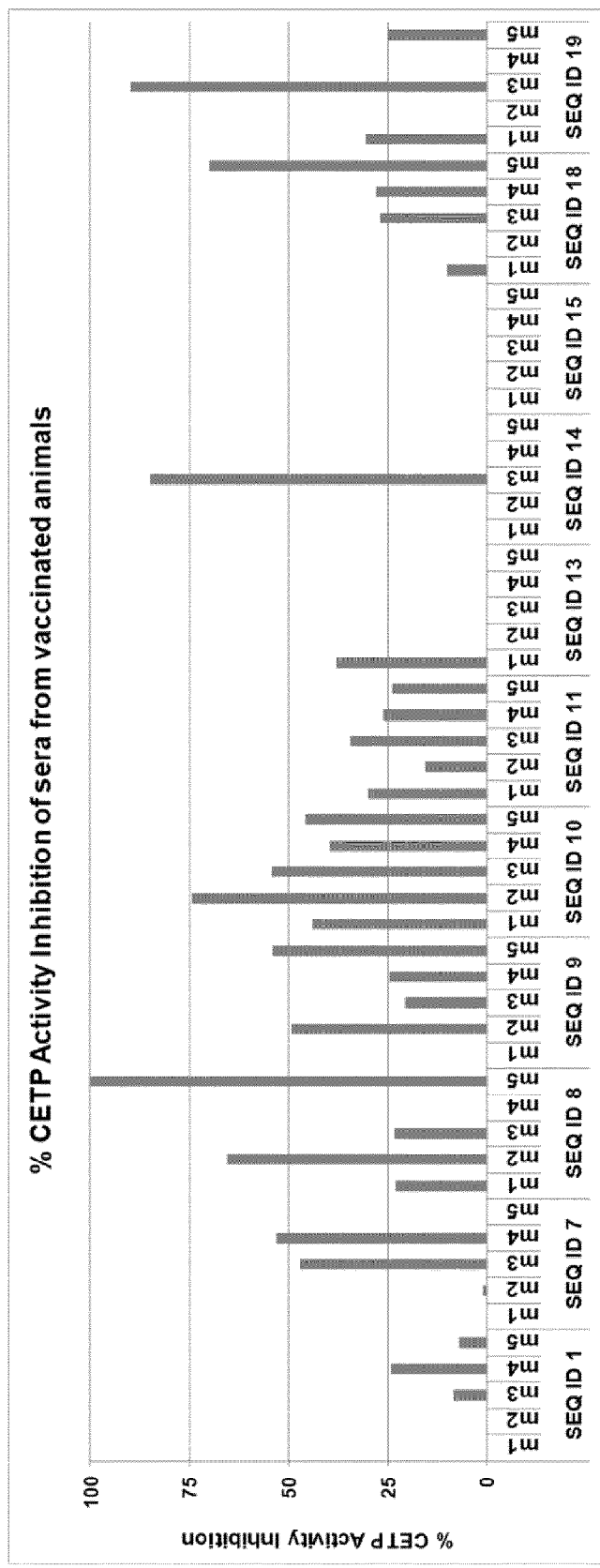
FIG. 4 shows the percent CETP activity inhibition of sera from mice (n=5 mice per group) vaccinated with peptides having amino acid sequence SEQ ID No. 1, 7, 8, 9, 10, 11, 13, 14, 15, 18 and 19.

Median Antibody Titers to Injected Peptide and to CETP (See FIGS. 1A and 1B).

| | median values (n = 5) | |
|---|---|---|
| SEQ ID No. | anti-peptide titers | anti-protein titers |
| 1 | 70,000 | 800 |
| 2 | 66,000 | 0 |
| 3 | 97,000 | 50 |
| 4 | 140,000 | 0 |
| 5 | 100,000 | 100 |
| 6 | 69,000 | 0 |
| 22 | 229,000 | 0 |

These data clearly show that the administration of a peptide comprising or consisting of amino acid sequence SEQ ID No. 1 leads to the formation of not only antibodies directed to the peptide itself but also to the mature CETP protein. The administration of other CETP fragments did only induce the formation of antibodies directed to the respective fragment and not to the mature CETP protein.

Example 2

Comparison of Immune Response to SEQ ID No. 1 and Truncated Versions Thereof

| SEQ ID No. (truncated peptides) | SEQ ID NO: (full-length peptides) | amino acid sequence | position within the mature CETP protein |
|---|---|---|---|
| 1 | 113 | C-YTTAWWLGIDQS | AA101-112 |
| 7 | 114 | C-YGYTTAWWLGIDQSID | AA99-114 |
| 8 | 115 | C-TTAWWLGIDQS | AA102-112 |
| 9 | 116 | C-TAWWLGIDQS | AA103-112 |
| 10 | 117 | C-AWWLGIDQS | AA104-112 |
| 11 | 118 | C-WWLGIDQS | AA105-112 |
| 12 | 129 | C-WLGIDQS | AA106-112 |
| 13 | 119 | C-YTTAWWLGIDQ | AA101-111 |
| 14 | 120 | C-YTTAWWLGID | AA101-110 |
| 15 | 130 | C-YTTAWWLGI | AA101-109 |
| 16 | 131 | C-YTTAWWLG | AA101-108 |
| 17 | 132 | C-YTTAWWL | AA101-107 |
| 18 | 121 | C-TTAWWLGIDQ | AA102-111 |
| 19 | 122 | TTAWWLGID-C | AA102-110 |
| 20 | 133 | C-TTAWWLGI | AA102-109 |
| 21 | 134 | C-TAWWLGI | AA102-108 |

Median Antibody Titers to Injected Peptide and to CETP as Well as Number of Mice with Antibodies Decreasing CETP Activity of Human Serum and Percent CETP Activity Inhibition in Human Serum Upon Addition of Sera from Single Vaccinated Mice (See FIGS. 2A, 2B, 3 and 4).

| | median values (n = 5) | |
|---|---|---|
| SEQ ID No. | anti-peptide titers | anti-protein titers |
| 1 | 70,000 | 800 |
| 7 | 33,000 | 500 |
| 8 | 89,000 | 1,200 |
| 9 | 173,000 | 2,200 |
| 10 | 191,000 | 1,700 |
| 11 | 330,000 | 1,100 |
| 12 | 153,000 | 0 |
| 13 | 143,000 | 1,200 |
| 14 | 630,000 | 600 |
| 15 | 111,000 | 300 |
| 16 | 74,000 | 0 |
| 17 | 94,000 | 0 |
| 18 | 216,000 | 900 |
| 19 | 114,000 | 1,300 |
| 20 | 124,000 | 300 |
| 21 | 99,000 | 0 |

These data revealed that CETP fragments comprising WWLGID (SEQ ID No. 24) are able to induce the formation of antibodies directed to mature CETP. In contrast thereto other CETP fragments derived from SEQ ID No. 23 which do not comprise amino acid sequence SEQ ID No. 24 did not show these effects.

Example 3

Inhibition of the CETP Activity

| SEQ ID No. | no. of mice with antibodies inhibiting CETP activity |
|---|---|
| 1 | 3 of 5 |
| 7 | 3 of 5 |
| 8 | 4 of 5 |
| 9 | 4 of 5 |
| 10 | 5 of 5 |
| 11 | 5 of 5 |
| 12 | n.t. |
| 13 | 1 of 5 |
| 14 | 1 of 5 |
| 15 | 0 of 5 |
| 16 | n.t. |
| 17 | n.t. |
| 18 | 4 of 5 |
| 19 | 3 of 5 |
| 20 | n.t. |
| 21 | n.t. | n.t. not tested because of low anti-protein titers

Example 4

Monoclonal Antibodies

Balb/c mice were vaccinated with 15 μg net peptide Seq ID No. 10 coupled to KLH. Alhydrogel was used as adjuvant. Spleen cells of mice with high anti-CETP protein titers were fused with mouse myeloma cells according to standard techniques (protocol adapted from Kohler, G. and Milstein, C. Nature. 256 (1975): 495-497). Hybridoma clones were tested in standard ELISAs for the production of antibodies specifically recognizing the injected peptide as wells as recombinantly expressed human CETP protein. Selected clones were cultured and monoclonal antibodies were purified from tissue culture supernatants according to standard protocols.

Sequencing of Monoclonal Antibodies:

RNA was extracted from hybridoma cells and cDNA was created by reverse transcription with an oligo(dT) primer. Subsequently PCR reactions using variable domain primers to amplify both the VH and VL regions of the monoclonal antibody DNA were performed. The VH and VL products were extracted and gel purified and cloned into a sequencing vector and transformed into TOP10. Selected colonies were picked and analyzed through sequencing.

Data from Four Selected Monoclonal Antibodies:

clones CJ7-6-B7, 5/C7-6-C8, 12/B3-5-B11, and BTS4-1.

Human CETP protein ELISA and CETP activity inhibition were performed as described above.

Figure 5:
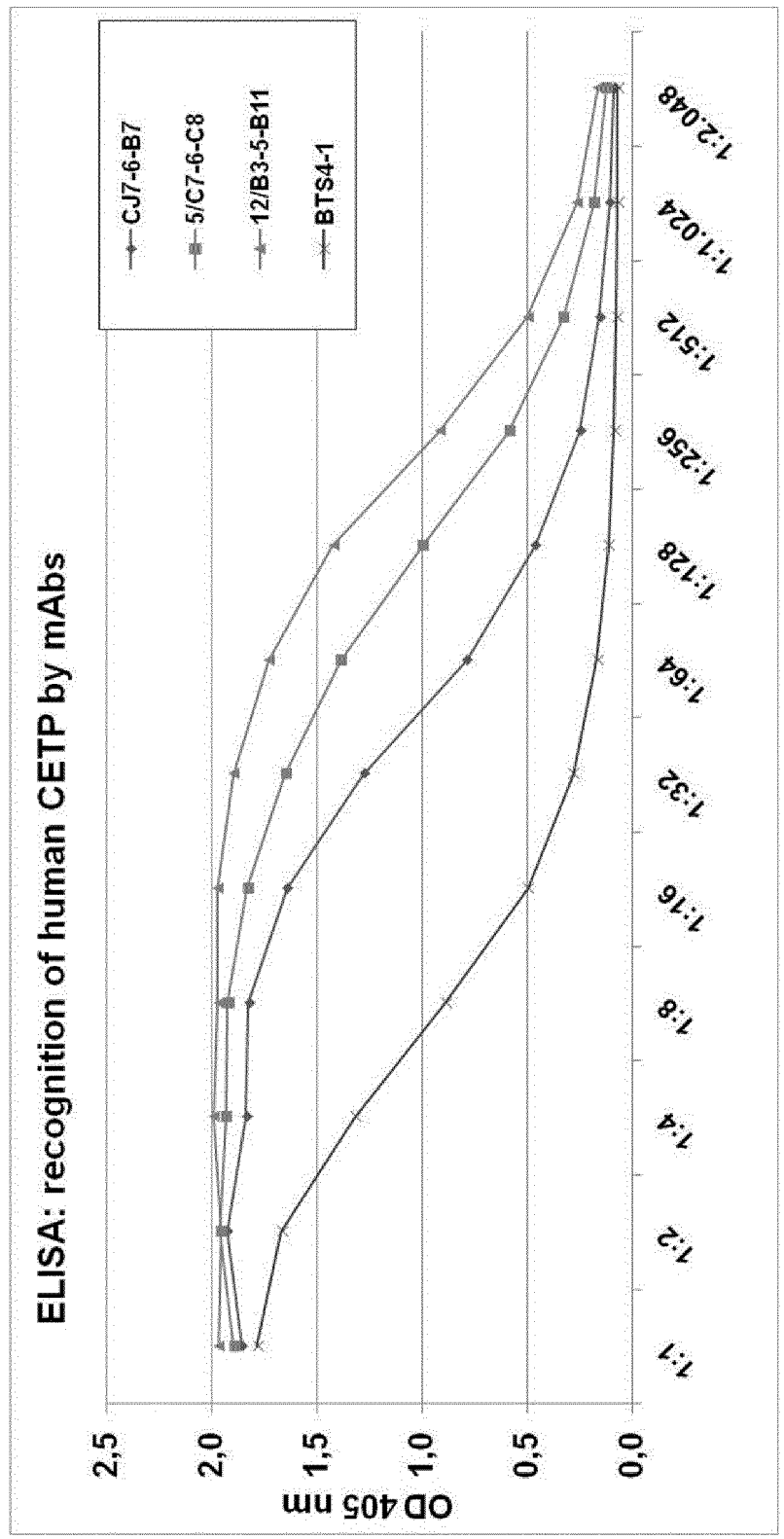
FIG. 5 shows the recognition of human CETP protein by the monoclonal antibodies of the present invention.

Recognition of Human CETP Protein by Monoclonal Antibodies (See FIG. 5).

These data revealed that all 4 antibodies are recognizing coated CETP protein. Titration in the ELISA was started with same amounts for all antibodies (2 mg/ml dilution). As expected, monoclonal antibodies differ in their ELISA signal which might be explained by different affinities to the coated protein.

Figure 6:
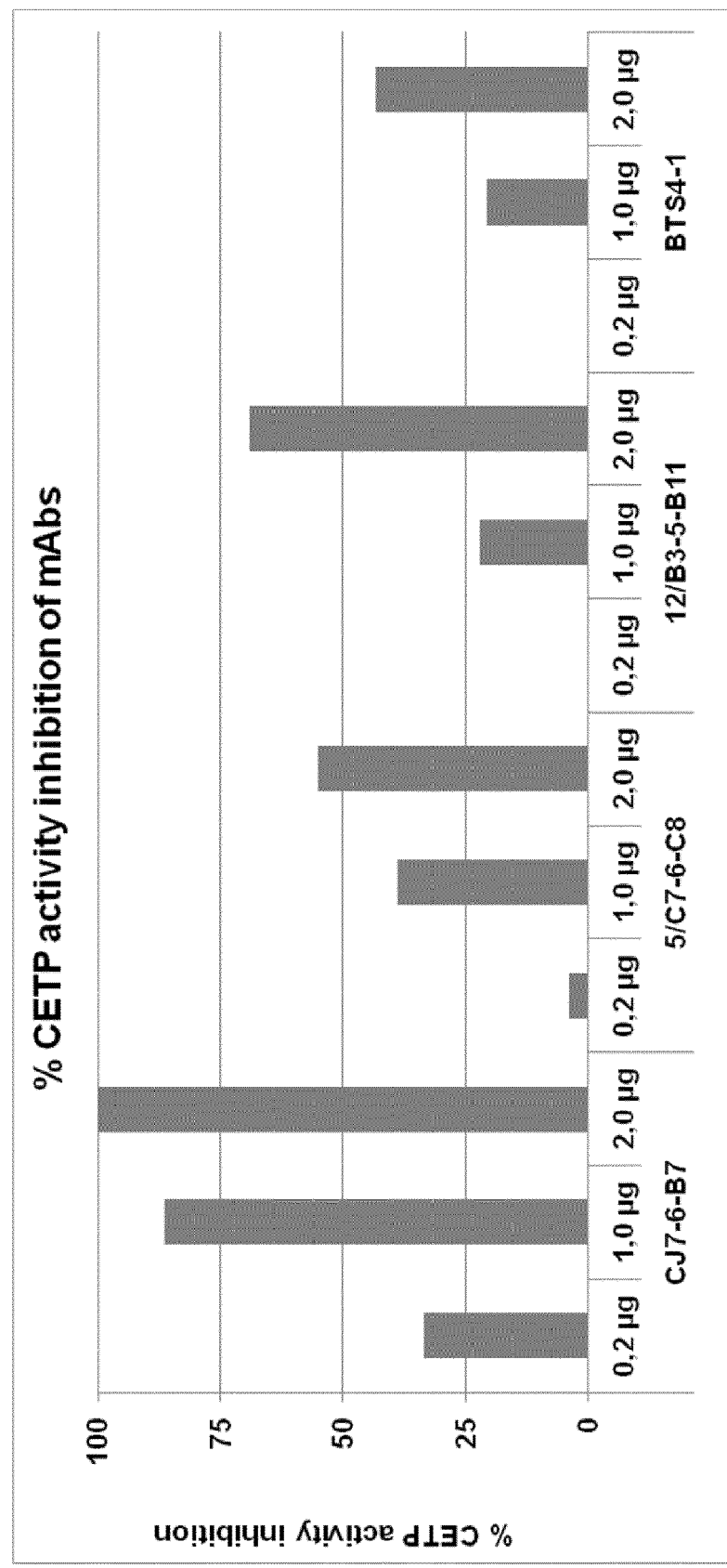
FIG. 6 shows the inhibition of CETP activity in human serum by the monoclonal antibodies according to the present invention.

Inhibition of CETP Activity in Human Serum by Monoclonal antibodies (See FIG. 6).

These data revealed that all 4 antibodies are not only binding to CETP but also inhibiting CETP activity. The higher the amount of antibody added, the more lowering of CETP activity is observed.

Sequences of Monoclonal Antibodies (Only the Variable domains are Given):

CJ7-6-B7
Heavy Chain:
(SEQ ID NO: 104)
NVQLQESGPGLVKPSQSLSLTCTVTGHSITSDYAWNWIRQFPGNKLEWMG

YITNSGSTTYNPSLKSRISITRDTSKNQFFLQLNSVTTEDTATYYCTRGG

PYWGQGTLVTVSA

Light Chain:
(SEQ ID NO: 108)
DIVMTQSQKFMSTSVGDRVSITCKASQNVGTAVVWYQQKPGQSPKLLIYS

ASNRYTGVPDRFTGSGSGTDFTLTITNMQSEDLADYFCQQYSSYPLTFGA

GTKLELK

5C7-6-C8
Heavy Chain:
(SEQ ID NO: 105)
EVQLVESGGGLVEPGGSLKLSCVASGFTFSTYAMSWFRLTPERRLEWVAA

ISNGGSQNSYPDSVKGRFTVSRDNAKNTLYLQMSSLRSEDTAMYYCSRNG

NYFDYWGQGTTLTVSS

Light Chain
(SEQ ID NO: 109)
QIVLTQSPAIMSASPGEKVTMTCSASSSISYMHWYQQKPGTSPKRWIFDT

SKLASGVPARFSGSGSGTSYSLTISSMEAEDAATYYCHQRSSYPTFGSGT

KLEIK

12B3-5-B11
Heavy Chain:
(SEQ ID NO: 106)
DVQLQESGPGLVKPSQSLSLTCTVTGYSITSDYAWNWIRQFPGNKLEWMG

YISYSGTTTYNPSLKSRISITRHTSKNQFFLQLNSVTTEDSATYYCTRLG

YYFDYWGQGTTLTVSS

Light Chain
(SEQ ID NO: 110)
DIVMTQSPASLAMSVGQKVTMNCKSSQSLLSSKNQKNFLAWYQQKPGQSP

KVLVYFASTRASGVPDRFIGSGSGTDFTLTISSVQAEDLADYFCQQQYNT

PLTFGAGTKLELK

BTS4-1
Heavy Chain:
(SEQ ID NO: 107)
QIQLVQSGPELKKPGETVKISCKASGYTFTDCSMHWVKQAPGQGLKWMG

WINTKTGEPTYADDFKGRFAFSLETSASTAYLQINILKNEDSATYFCAA

HSGKDYAIDYWGQGTSVTVSS

Light Chain
(SEQ ID NO: 111)
DVLMTQTPLSLPVSLGDQASISCRSSQSIVHRNGNTYLEWYLQKPGQSP

KLLIYKVSNRFSGVPDRFSGSGSGTDFTLRISRVEAQDLGVYFCFQGSR

VPPTFGGGTKLEIK

---

The invention claimed is:

1. A composition comprising an isolated peptide consisting of from 6 to 20 amino acid residues, the peptide coupled or fused to a pharmaceutically acceptable carrier,
wherein the peptide is derived from the amino acid sequence VFKGTLKYGYTTAWWLGIDQSID-FEIDSAI (SEQ ID No. 23), and comprises the amino acid sequence WWLGID (SEQ ID No. 24).

2. The composition according to claim 1, wherein an amino acid sequence of the peptide is selected from the group consisting of YTTAWWLGIDQS (SEQ ID No. 1), YGYTTAW-WLGIDQSID (SEQ ID No. 7), TTAWWLGIDQS (SEQ ID No. 8), TAWWLGIDQS (SEQ ID No. 9), AWWLGIDQS (SEQ ID No. 10), WWLGIDQS (SEQ ID No. 11), YTTAW-WLGIDQ (SEQ ID No. 13), YTTAWWLGID (SEQ ID No. 14), TTAWWLGIDQ (SEQ ID No. 18), and TTAWWLGID (SEQ ID No. 19).

3. The composition according to claim 1, wherein the peptide comprises a cysteine residue at a terminus of at least one of a C-terminus and a N-terminus.

4. The composition according to claim 1, wherein the peptide is suitable for preventing, treating, or both preventing and treating atherosclerosis and a disease associated with atherosclerosis.

5. The composition according to claim 4, wherein the disease associated with atherosclerosis is selected from the group consisting of peripheral arterial occlusive disease, coronary heart disease, apoplectic cerebral insultus and stroke.

6. The composition according to claim 1, wherein the peptide is formulated for intradermal, subcutaneous or intramuscular administration.

7. The composition according to claim 1, further comprising an adjuvant.

8. The composition according to claim 7, wherein the adjuvant is aluminum hydroxide.

9. The composition according to claim 1, wherein the peptide is present in an amount of 0.5 to 500 μg.

10. The composition according to claim 1, wherein the pharmaceutically acceptable carrier is Keyhole Limpet Hemocyanin.

11. The composition according to claim 1, wherein the peptide consists of from 7 to 21 amino acid residues.

12. The composition according to claim 1, wherein the peptide consists of from 8 to 22 amino acid residues.

* * * * *

SEQUENCE LISTING

```
<160> NUMBER OF SEQ ID NOS: 134

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 1

Tyr Thr Thr Ala Trp Trp Leu Gly Ile Asp Gln Ser
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
```

CETP fragment peptide

<400> SEQUENCE: 2

Lys Ala Met Met Leu Leu Gly Gln Val
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 3

Leu His Leu Gln Gly Glu Arg Glu Pro Gly Trp Ile Lys Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 4

Asp Glu Phe Lys Ala Val Leu Glu Thr Trp Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 5

Gly Phe Asn Thr Asn Gln Glu Ile Phe Gln Glu Val Val Gly Gly Phe
1               5                   10                  15

Pro

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 6

Glu Ser Ile Gln Ser Phe Leu Gln Ser Met Ile Thr Ala
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 7

Tyr Gly Tyr Thr Thr Ala Trp Trp Leu Gly Ile Asp Gln Ser Ile Asp
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 8

Thr Thr Ala Trp Trp Leu Gly Ile Asp Gln Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 9

Thr Ala Trp Trp Leu Gly Ile Asp Gln Ser
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 10

Ala Trp Trp Leu Gly Ile Asp Gln Ser
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 11

Trp Trp Leu Gly Ile Asp Gln Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 12

Trp Leu Gly Ile Asp Gln Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      CETP fragment peptide

```
<400> SEQUENCE: 13

Tyr Thr Thr Ala Trp Trp Leu Gly Ile Asp Gln
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 14

Tyr Thr Thr Ala Trp Trp Leu Gly Ile Asp
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 15

Tyr Thr Thr Ala Trp Trp Leu Gly Ile
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 16

Tyr Thr Thr Ala Trp Trp Leu Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 17

Tyr Thr Thr Ala Trp Trp Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 18

Thr Thr Ala Trp Trp Leu Gly Ile Asp Gln
1               5                   10

<210> SEQ ID NO 19
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      CETP fragment peptide

<400> SEQUENCE: 19

Thr Thr Ala Trp Trp Leu Gly Ile Asp
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 20

Thr Thr Ala Trp Trp Leu Gly Ile
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 21

Thr Ala Trp Trp Leu Gly Ile
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 22

Phe Pro Arg Pro Asp Gln Gln His Ser Val
1               5                   10

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Phe Lys Gly Thr Leu Lys Tyr Gly Tyr Thr Thr Ala Trp Trp Leu
1               5                   10                  15

Gly Ile Asp Gln Ser Ile Asp Phe Glu Ile Asp Ser Ala Ile
            20                  25                  30

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      CETP fragment peptide

<400> SEQUENCE: 24
```

```
Trp Trp Leu Gly Ile Asp
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala, Phe, Tyr or Lys
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (5)..(5)
<223> OTHER INFORMATION: Glu, Tyr, Ala, Gln, Lys or Ser
<220> FEATURE:
<221> NAME/KEY: MOD_RES
<222> LOCATION: (7)..(7)
<223> OTHER INFORMATION: His, Val, Leu, Phe or Ile
<220> FEATURE:
<221> NAME/KEY: MOD_RES
<222> LOCATION: (8)..(8)
<223> OTHER INFORMATION: Leu, Trp, Ser, Ile, Phe or Tyr
<220> FEATURE:
<221> NAME/KEY: MOD_RES
<222> LOCATION: (9)..(9)
<223> OTHER INFORMATION: Val, Thr, Phe or Ile
<220> FEATURE:
<221> NAME/KEY: MOD_RES
<222> LOCATION: (11)..(11)
<223> OTHER INFORMATION: Phe, Ala, Trp, Arg, Ser, Leu, Gln, Val or Met
<220> FEATURE:
<221> NAME/KEY: MOD_RES
<222> LOCATION: (12)..(12)
<223> OTHER INFORMATION: Leu, Ala, Ser, Trp, Glu, Arg, Ile or His
<220> FEATURE:
<221> NAME/KEY: MOD_RES
<222> LOCATION: (13)..(13)
<223> OTHER INFORMATION: Gln, Ala, His, Asp, Lys, Arg, Ser or Glu
<220> FEATURE:
<221> NAME/KEY: MOD_RES
<222> LOCATION: (14)..(14)
<223> OTHER INFORMATION: Ser or Tyr
<220> FEATURE:
<221> NAME/KEY: MOD_RES
<222> LOCATION: (15)..(15)
<223> OTHER INFORMATION: Leu, Ala or Ile
<220> FEATURE:
<221> NAME/KEY: MOD_RES
<222> LOCATION: (16)..(16)
<223> OTHER INFORMATION: Ser, Asn or Thr

<400> SEQUENCE: 25

Phe Xaa Phe Pro Xaa His Xaa Xaa Xaa Asp Xaa Xaa Xaa Xaa Xaa Xaa
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 26

Phe Gly Phe Pro Glu His Leu Leu Val Asp Phe Leu Gln Ser Leu Ser
1               5                   10                  15
```

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 27

Phe Pro Glu His Leu Leu Val Asp Phe Leu Gln Ser Leu
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 28

Ala Gly Phe Pro Glu His Leu Leu Val Asp Phe Leu Gln Ser Leu Ser
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 29

Phe Ala Phe Pro Glu His Leu Leu Val Asp Phe Leu Gln Ser Leu Ser
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 30

Phe Gly Ala Pro Glu His Leu Leu Val Asp Phe Leu Gln Ser Leu Ser
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 31

Phe Gly Phe Ala Glu His Leu Leu Val Asp Phe Leu Gln Ser Leu Ser
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 32

Phe Gly Phe Pro Ala His Leu Leu Val Asp Phe Leu Gln Ser Leu Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 33

Phe Gly Phe Pro Glu Ala Leu Leu Val Asp Phe Leu Gln Ser Leu Ser
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 34

Phe Gly Phe Pro Glu His Ala Leu Val Asp Phe Leu Gln Ser Leu Ser
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 35

Phe Gly Phe Pro Glu His Leu Ala Val Asp Phe Leu Gln Ser Leu Ser
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 36

Phe Gly Phe Pro Glu His Leu Leu Ala Asp Phe Leu Gln Ser Leu Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 37

Phe Gly Phe Pro Glu His Leu Leu Val Ala Phe Leu Gln Ser Leu Ser
1               5                   10                  15

<210> SEQ ID NO 38
<211> LENGTH: 16

```
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 38

Phe Gly Phe Pro Glu His Leu Leu Val Asp Ala Leu Gln Ser Leu Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 39

Phe Gly Phe Pro Glu His Leu Leu Val Asp Phe Ala Gln Ser Leu Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 40

Phe Gly Phe Pro Glu His Leu Leu Val Asp Phe Leu Ala Ser Leu Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 41

Phe Gly Phe Pro Glu His Leu Leu Val Asp Phe Leu Gln Ala Leu Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 42

Phe Gly Phe Pro Glu His Leu Leu Val Asp Phe Leu Gln Ser Ala Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 43

Phe Gly Phe Pro Glu His Leu Leu Val Asp Phe Leu Gln Ser Leu Ala
```

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 44

Phe Ala Phe Pro Ala His Leu Leu Val Asp Phe Leu Gln Ala Leu Ala
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 45

Phe Gly Phe Pro Gly His Leu Ile Trp Asp Ser Leu His Ser Leu Ser
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 46

Phe Gly Phe Pro Tyr His His Leu Val Asp Gln Leu His Ser Leu Ser
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 47

Phe Gly Phe Pro Tyr His Val Gln Val Asp Val Leu Gln Ser Leu Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 48

Phe Gly Phe Pro Ser His His Leu Gln Asp Ser Leu Gln Ser Leu Ser
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic -continued mimotope peptide of a CETP fragment

<400> SEQUENCE: 49

Phe Gly Phe Pro Leu His Phe Arg Ser Asp Arg Ile Gln Ser Leu Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 50

Phe Gly Phe Pro Lys His Leu Tyr Ala Asp Met Ser Gln Ser Leu Ser
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 51

Phe Gly Phe Pro Ala His Leu Ser Arg Asp Leu Arg Gln Ser Leu Ser
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 52

Phe Gly Phe Pro Phe His Phe Ala Gln Asp Ser Trp Gln Ser Leu Ser
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 53

Phe Gly Phe Pro Gln His Leu Thr Thr Asp Arg Ala Gln Ser Leu Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 54

Phe Gly Phe Pro Gln His Leu Thr Thr Asp Trp Ala Gln Ser Leu Ser
1               5                   10                  15

<210> SEQ ID NO 55

```
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 55

Phe Gly Phe Pro Gln His Leu Thr Thr Asp Arg Leu Gln Ser Leu Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 56

Phe Gly Phe Pro Gln His Leu Thr Thr Asp Trp Leu Gln Ser Leu Ser
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 57

Ala Thr Pro Ser His Leu Ile Ile Asp Arg Ala Gln
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 58

Ala Thr Pro Ser His Leu Ile Ile Asp Arg Ala Gln Ser Leu Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 59

Phe Gly Phe Pro Ser His Leu Ile Ile Asp Arg Ala Gln Ser Leu Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 60
```

```
Phe Gly Phe Pro Ser His Leu Ile Ile Asp Trp Ala Gln Ser Leu Ser
1               5                   10                  15
```

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 61

```
Phe Gly Phe Pro Ser His Leu Ile Ile Asp Trp Leu Gln Ser Leu Ser
1               5                   10                  15
```

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 62

```
Phe Gly Phe Pro Ser His Leu Ile Ile Asp Trp Ser Gln Ser Leu Ser
1               5                   10                  15
```

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 63

```
Phe Ala Phe Pro Ala His Val Ser Ile Asp Trp Leu Gln Ser Leu Ser
1               5                   10                  15
```

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 64

```
Phe Gly Phe Pro Ala His Val Ser Ile Asp Trp Leu Gln Leu Leu Ser
1               5                   10                  15
```

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 65

```
Phe Gly Phe Pro Ala His Val Ser Ile Asp Trp Leu Gln Trp Leu Ser
1               5                   10                  15
```

<210> SEQ ID NO 66
<211> LENGTH: 16
<212> TYPE: PRT
<213> ORGANISM: Artificial Sequence
<220> FEATURE:

```
<223> OTHER INFORMATION: Description of Artificial Sequence: Synthetic
      mimotope peptide of a CETP fragment

<400> SEQUENCE: 66

Phe Gly Phe Pro Ala His Val Ser Ile Asp Trp Leu Gln Asn Leu Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 67

Phe Gly Phe Pro Ala His Val Ser Ile Asp Trp Leu Gln Thr Leu Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 68

Phe Gly Phe Pro Ala His Val Ser Ile Asp Trp Leu Gln Tyr Leu Ser
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 69

Phe Gly Phe Pro Ala His Val Ser Ile Asp Trp Leu Gln Ser Ile Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 70

Phe Gly Phe Pro Ala His Val Ser Ile Asp Trp Leu Gln Ser Leu Thr
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 71

Phe Gly Phe Pro Ala His Val Ser Ile Asp Trp Leu Gln Ser Leu Tyr
1               5                   10                  15
```

-continued

```
<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 72

Phe Ala Phe Pro Ala His Val Ser Ile Asp Trp Leu Gln Ala Leu Ala
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 73

Phe Gly Phe Pro Ala His Val Ser Ile Asp Arg Ala Gln Ser Leu Ser
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 74

Phe Gly Phe Pro Thr His Val Ser Ile Asp Trp Leu Gln Ser Leu Ser
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 75

Phe Gly Phe Pro Phe His Val Ser Ile Asp Trp Leu Gln Ser Leu Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 76

Phe Gly Phe Pro Ala His Ile Ser Ile Asp Trp Leu Gln Ser Leu Ser
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 77
```

```
Phe Gly Phe Pro Ala His Ile Ile Ile Asp Trp Leu Gln Ser Leu Ser
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 78

Phe Gly Phe Pro Ala His Leu Thr Thr Asp Trp Leu Gln Ser Leu Ser
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 79

Phe Gly Phe Pro Ala His Val Phe Ile Asp Trp Leu Gln Ser Leu Ser
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 80

Phe Gly Phe Pro Ala His Val Tyr Ile Asp Trp Leu Gln Ser Leu Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 81

Phe Gly Phe Pro Ala His Val Ser Leu Asp Trp Leu Gln Ser Leu Ser
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 82

Phe Gly Phe Pro Ala His Val Ser Ala Asp Trp Leu Gln Ser Leu Ser
1               5                   10                  15

<210> SEQ ID NO 83
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      mimotope peptide of a CETP fragment

<400> SEQUENCE: 83

Phe Gly Phe Pro Ala His Val Trp Ile Asp Trp Leu Gln Ser Leu Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 84

Phe Gly Phe Pro Ala His Val Phe Ile Asp Trp Leu Gln Ser Leu Asn
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 85

Phe Gly Phe Pro Ala His Phe Ser Ile Asp Trp Leu Gln Ser Leu Ser
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 86

Phe Gly Phe Pro Ala His Val Ser Phe Asp Trp Leu Gln Ser Leu Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 87

Phe Gly Phe Pro Glu His Val Phe Ile Asp Trp Leu Gln Ser Leu Ser
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 88

Phe Gly Phe Pro Gln His Leu Phe Thr Asp Trp Leu Gln Ser Leu Ser
1               5                   10                  15
```

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 89

Phe Gly Phe Pro Lys His Leu Leu Val Asp Phe Leu Gln Ser Leu Ser
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 90

Phe Gly Phe Pro Ala His Val Ser Ile Asp Trp Ser Gln Ser Leu Ser
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 91

Phe Gly Phe Pro Ala His Val Ser Ile Asp Phe Ser Gln Ser Leu Ser
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 92

Phe Gly Phe Pro Ser His Ile Ile Ile Asp Trp Leu Gln Ser Leu Ser
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 93

Phe Gly Phe Pro Ser His Leu Ile Ile Glu Trp Leu Gln Ser Leu Ser
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

```
<400> SEQUENCE: 94

Phe Ala Phe Pro Ala His Val Phe Ile Asp Trp Leu Gln Ser Leu Ser
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 95

Phe Gly Phe Pro Ala His Val Phe Ile Asp Trp Leu Gln Ala Leu Ser
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 96

Phe Gly Phe Pro Ala His Val Phe Ile Asp Trp Leu Gln Ser Leu Ala
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 97

Phe Ala Phe Pro Ala His Val Phe Ile Asp Trp Leu Gln Ala Leu Ala
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 98

Phe Gly Phe Pro Glu His Leu Phe Val Asp Phe Leu Gln Ser Leu Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      mimotope peptide of a CETP fragment

<400> SEQUENCE: 99

Phe Gly Phe Pro Ala His Val His Ile Asp Trp Leu Gln Ser Leu Ser
1               5                   10                  15

<210> SEQ ID NO 100
<211> LENGTH: 16
<212> TYPE: PRT
```

<213> ORGANISM: Artificial Sequence
<220> FEATURE:
<223> OTHER INFORMATION: Description of Artificial Sequence: Synthetic mimotope peptide of a CETP fragment

<400> SEQUENCE: 100

Phe Gly Phe Pro Ala His Val Pro Ile Asp Trp Leu Gln Ser Leu Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic mimotope peptide of a CETP fragment

<400> SEQUENCE: 101

Phe Gly Phe Pro Ser His Leu Phe Ile Asp Trp Ala Gln Ser Leu Ser
1               5                   10                  15

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic mimotope peptide of a CETP fragment

<400> SEQUENCE: 102

Phe Gly Phe Pro Ala His Val Tyr Ile Asp Trp Leu Gln
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic mimotope peptide of a CETP fragment

<400> SEQUENCE: 103

Phe Gly Phe Pro Ala His Val Phe Ile Asp Trp Leu Gln
1               5                   10

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Asn Val Gln Leu Gln Glu Ser Gly Pro Gly Leu Val Lys Pro Ser Gln
1               5                   10                  15

Ser Leu Ser Leu Thr Cys Thr Val Thr Gly His Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Asn Ser Gly Ser Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys

```
                85                  90                  95
Thr Arg Gly Gly Pro Tyr Trp Gly Gln Gly Thr Leu Val Thr Val Ser
            100                 105                 110
Ala

<210> SEQ ID NO 105
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Val Glu Pro Gly Gly
1               5                   10                  15

Ser Leu Lys Leu Ser Cys Val Ala Ser Gly Phe Thr Phe Ser Thr Tyr
            20                  25                  30

Ala Met Ser Trp Phe Arg Leu Thr Pro Glu Arg Arg Leu Glu Trp Val
        35                  40                  45

Ala Ala Ile Ser Asn Gly Gly Ser Gln Asn Ser Tyr Pro Asp Ser Val
    50                  55                  60

Lys Gly Arg Phe Thr Val Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ser Arg Asn Gly Asn Tyr Phe Asp Tyr Trp Gly Gln Gly Thr Thr Leu
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Thr Tyr Asn Pro Ser Leu
    50                  55                  60

Lys Ser Arg Ile Ser Ile Thr Arg His Thr Ser Lys Asn Gln Phe Phe
65                  70                  75                  80

Leu Gln Leu Asn Ser Val Thr Thr Glu Asp Ser Ala Thr Tyr Tyr Cys
                85                  90                  95

Thr Arg Leu Gly Tyr Tyr Phe Asp Tyr Trp Gly Gln Gly Thr Thr Leu
            100                 105                 110

Thr Val Ser Ser
        115

<210> SEQ ID NO 107
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Cys
            20                  25                  30

Ser Met His Trp Val Lys Gln Ala Pro Gly Gln Gly Leu Lys Trp Met
        35                  40                  45

Gly Trp Ile Asn Thr Lys Thr Gly Glu Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ile Leu Lys Asn Glu Asp Ser Ala Thr Tyr Phe Cys
                85                  90                  95

Ala Ala His Ser Gly Lys Asp Tyr Ala Ile Asp Tyr Trp Gly Gln Gly
            100                 105                 110

Thr Ser Val Thr Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Val Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 109
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Ile Val Leu Thr Gln Ser Pro Ala Ile Met Ser Ala Ser Pro Gly
1               5                   10                  15
```

```
Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Phe
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                 70                  75                  80

Asp Ala Ala Thr Tyr Tyr Cys His Gln Arg Ser Ser Tyr Pro Thr Phe
                85                  90                  95

Gly Ser Gly Thr Lys Leu Glu Ile Lys
            100                 105

<210> SEQ ID NO 110
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Pro Ala Ser Leu Ala Met Ser Val Gly
 1               5                  10                  15

Gln Lys Val Thr Met Asn Cys Lys Ser Ser Gln Ser Leu Leu Ser Ser
            20                  25                  30

Lys Asn Gln Lys Asn Phe Leu Ala Trp Tyr Gln Gln Lys Pro Gly Gln
        35                  40                  45

Ser Pro Lys Val Leu Val Tyr Phe Ala Ser Thr Arg Ala Ser Gly Val
    50                  55                  60

Pro Asp Arg Phe Ile Gly Ser Gly Ser Gly Thr Asp Phe Thr Leu Thr
 65                 70                  75                  80

Ile Ser Ser Val Gln Ala Glu Asp Leu Ala Asp Tyr Phe Cys Gln Gln
                85                  90                  95

Gln Tyr Asn Thr Pro Leu Thr Phe Gly Ala Gly Thr Lys Leu Glu Leu
            100                 105                 110

Lys

<210> SEQ ID NO 111
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
 65                 70                  75                  80

Ser Arg Val Glu Ala Gln Asp Leu Gly Val Tyr Phe Cys Phe Gln Gly
```

```
                    85                  90                  95
Ser Arg Val Pro Pro Thr Phe Gly Gly Gly Thr Lys Leu Glu Ile Lys
            100                 105                 110

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 112

His His His His His His
1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Tyr Thr Thr Ala Trp Trp Leu Gly Ile Asp Gln Ser
1               5                   10

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Tyr Gly Tyr Thr Thr Ala Trp Trp Leu Gly Ile Asp Gln Ser Ile
1               5                   10                  15

Asp

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Thr Ala Trp Trp Leu Gly Ile Asp Gln Ser
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Thr Ala Trp Trp Leu Gly Ile Asp Gln Ser
1               5                   10

<210> SEQ ID NO 117
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Ala Trp Trp Leu Gly Ile Asp Gln Ser
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Trp Trp Leu Gly Ile Asp Gln Ser
1               5

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Cys Tyr Thr Thr Ala Trp Trp Leu Gly Ile Asp Gln
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Tyr Thr Thr Ala Trp Trp Leu Gly Ile Asp
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Thr Thr Ala Trp Trp Leu Gly Ile Asp Gln
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
Thr Thr Ala Trp Trp Leu Gly Ile Asp Cys
1               5                   10
```

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Cys Lys Ala Met Met Leu Leu Gly Gln Val
1               5                   10
```

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Cys Leu His Leu Gln Gly Glu Arg Glu Pro Gly Trp Ile Lys Gln
1               5                   10                  15
```

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Cys Asp Glu Phe Lys Ala Val Leu Glu Thr Trp Gly
1               5                   10
```

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Cys Gly Phe Asn Thr Asn Gln Glu Ile Phe Gln Glu Val Val Gly Gly
1               5                   10                  15

Phe Pro
```

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Cys Glu Ser Ile Gln Ser Phe Leu Gln Ser Met Ile Thr Ala
1               5                   10
```

<210> SEQ ID NO 128
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 128

Cys Phe Pro Arg Pro Asp Gln Gln His Ser Val
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Trp Leu Gly Ile Asp Gln Ser
1               5

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Tyr Thr Thr Ala Trp Trp Leu Gly Ile
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Tyr Thr Thr Ala Trp Trp Leu Gly
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Tyr Thr Thr Ala Trp Trp Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Thr Thr Ala Trp Trp Leu Gly Ile
1               5
```

```
<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Thr Ala Trp Trp Leu Gly Ile
1               5
```